(12) United States Patent
Lai

(10) Patent No.: US 8,455,196 B2
(45) Date of Patent: Jun. 4, 2013

(54) BIOMARKER FOR IDENTIFYING SUBGROUP OF EARLY-STAGE LUNG ADENOCARCINOMA PATIENTS

(76) Inventor: Jin-Mei Lai, Taipei (TW)

( * ) Notice: Subject to any disclaimer, the term of this patent is extended or adjusted under 35 U.S.C. 154(b) by 0 days.

(21) Appl. No.: 13/478,835

(22) Filed: May 23, 2012

(65) Prior Publication Data

US 2012/0302624 A1    Nov. 29, 2012

Related U.S. Application Data

(60) Provisional application No. 61/489,063, filed on May 23, 2011.

(51) Int. Cl.
*C12Q 1/68*    (2006.01)

(52) U.S. Cl.
USPC .......................................... 435/6.1; 424/900

(58) Field of Classification Search
None
See application file for complete search history.

(56) References Cited

U.S. PATENT DOCUMENTS

2005/0064402 A1*   3/2005   Goldsworthy et al. ........... 435/6

OTHER PUBLICATIONS

Zlobec et al, Prognostic and predictive value of TOPK stratified by KRAS and BRAF gene alterations in sporadic, hereditary and metastatic colorectal cancer patients, Nov. 2009, British Journal of Cancer, 102:151-161.*

* cited by examiner

*Primary Examiner* — Tracy Vivlemore
*Assistant Examiner* — Kate Poliakova
(74) *Attorney, Agent, or Firm* — WPAT, P.C.; Anthony King

(57) ABSTRACT

The preset invention relates to a biomarker for identifying the subgroup of early-stage lung adenocarcinoma patients in early-stage non-small cell lung cancer (NSCLC), which is T-lymphokine-activated killer cell-originated protein kinase (TOPK), and a therapeutic target for lung cancer.

3 Claims, 16 Drawing Sheets
(6 of 16 Drawing Sheet(s) Filed in Color)

(A)

(B)

(A)

(B)

(C)

ized by immu-
BIOMARKER FOR IDENTIFYING SUBGROUP OF EARLY-STAGE LUNG ADENOCARCINOMA PATIENTS This application claim benefit under 35 U.S.C 119(e) of U.S. Provisional Application No. 61/489,063, filed May 23, 2011, the entire content of which are incorporated by reference herein.

FIELD OF THE INVENTION

The present invention relates to a biomarker and method for identifying the subgroup of early-stage lung adenocarcinoma patients in early-stage NSCLC, which is helpful for the design of clinical trials for adjuvant therapy.

BACKGROUND OF THE INVENTION

Lung cancer is the leading cause of cancer-related death globally. For early-stage non-small cell lung cancer (NSCLC), a surgical resection is one of the choice for treatment of early-stage non-small cell lung cancer (NSCLC).[1,2] Although surgical resection remains the mainstay of the treatment and provides the best chance for survival,[3-6] the reported failure rate in stage I NSCLC ranges from 27% to 38%,[5-9] and about 90% cancer deaths are associated with tumor recurrence or metastasis.[8-12] Many randomized clinical trials have evaluated the role of adjuvant chemotherapy in patients with resected stage I NSCLC,[13-15] and tried to identify patients with higher risks of recurrence or poor prognosis after surgical resection. However, the results remain controversial.

It was found in the prior art references, the patients with stage I NSCLC had relative good outcome after surgical resection.[3-6] However, the survival in patients with recurrence after surgical resection was poor.[8-12] Adenocarcinoma was the most common histologic subtype of NSCLC in most countries.[28,29] Furthermore, adenocarcinoma increased in both sexes in the past decades while squamous cell carcinoma had decreased.[28] Although postoperative adjuvant chemotherapy was widely accepted in locally advanced NSCLC, the role of adjuvant chemotherapy in early-stage NSCLC remained to be determined. Many reports in the literature tried to identify poor prognostic factors in patients with stage I NSCLC for adjuvant therapy.[13-15] Furthermore, it was discovered in several current clinical trials that histologic subgroups had different outcomes to targeted therapy and newer chemotherapy.[30-33]

Therefore, to identify subgroup of early-stage lung adenocarcinoma patients with higher risks for histology-based treatment is important and still desirous in the early stage.

SUMMARY OF THE INVENTION

It is unexpectedly found in the invention that T-lymphocyte-activated killer cell-Originated Protein Kinase (TOPK) is a potential therapeutic target in lung cancer that promotes cell migration by modulating a PI3K/PTEN/AKT-dependent signaling pathway. Moreover, it is also found in the invention that knockdown TOPK can decrease lung cancer stem cells characteristics and sensitize cisplatin-induced lung cancer cell death. That is, the present invention provides a biomarker for identifying the subgroup of early-stage lung adenocarcinoma patients in early-stage NSCLC, which is T-lymphokine-activated killer cell-originated protein kinase (TOPK), and a therapeutic target for lung cancer.

Accordingly, in one aspect, the invention provides a method for identifying the subgroup of early-stage lung adenocarcinoma patients in an early-stage NSCLC patient, comprising collecting a tissue sample from the patient, determining the level of TOPK expressed in the tissue sample, and identifying the subgroup of early-stage lung adenocarcinoma patients based on the TOPK expression, wherein the overall survival of the patient is worse if the overexpression of TOPK in the patient's tissue sample is found.

In a further aspect, the invention provides a method for designing a clinical trial for the treatment of lung adenocarcinoma in early-stage NSCLC patients, comprising collecting a tissue samples from the patients, determining the level of TOPK expressed in the tissue samples, and sub-grouping the patients with the levels of survival in terms of the TOPK expression in the patients' tissue samples.

In yet further aspect, the present invention provides a method for evaluating the prognostic value in a patient in the resected stage I adenocarcinoma comprising collecting a tissue sample from the patient, determining the level of TOPK expressed in the tissue sample, and identifying the prognostic value of the patient based on the level of the TOPK expression, wherein the prognostic value of the patient is worse if the overexpression of TOPK in the patient's tissue sample is found.

In yet further aspect, the present invention provides a method for treating a cancer comprising administering a subject in need thereof a TOPK inhibitor at a therapeutically efficient amount to decrease cancer stem cells characteristics and sensitize cisplatin-induced cancer cell death.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings.

In the drawings:

Figure 1:
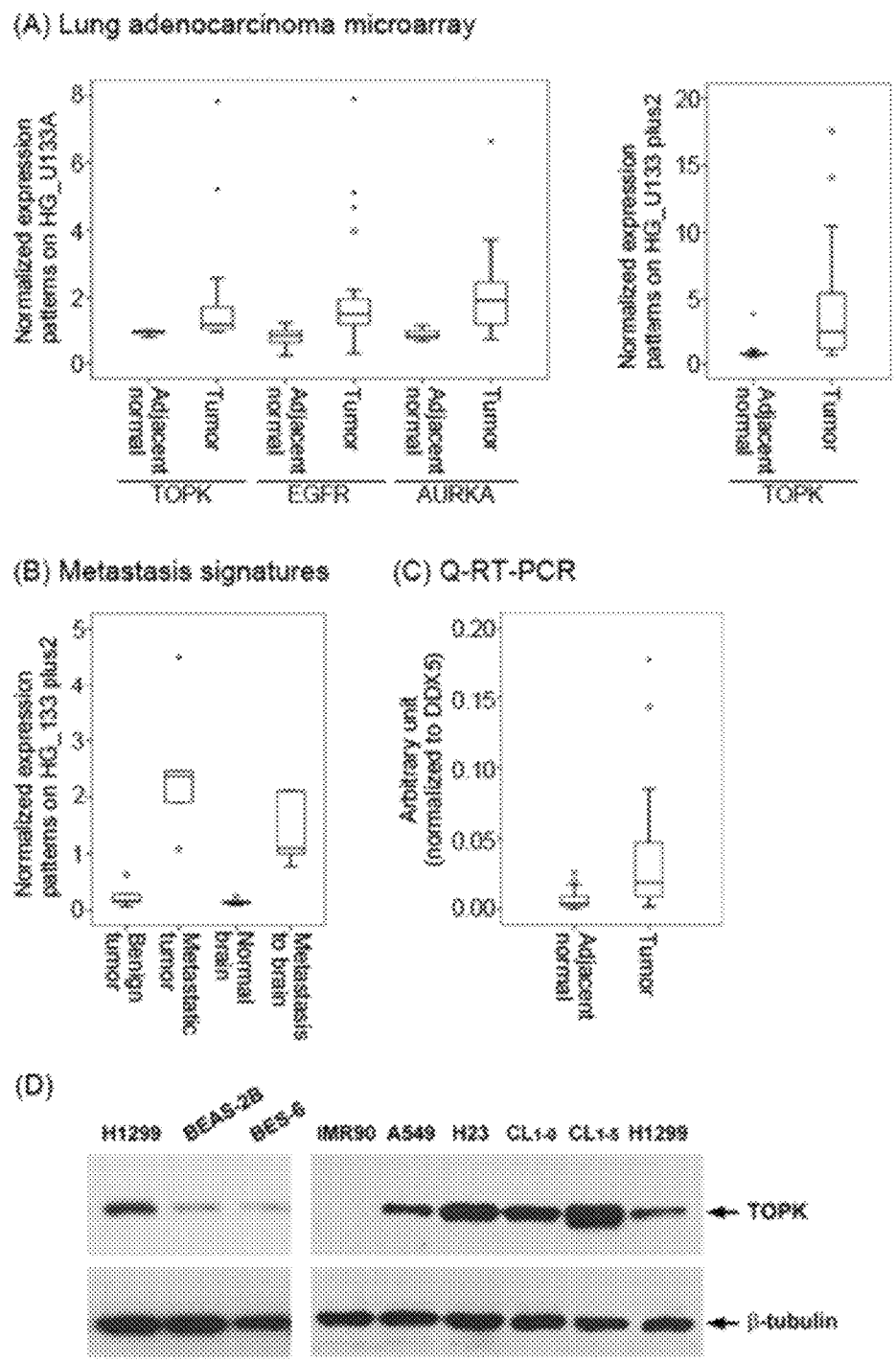
Figure 2:
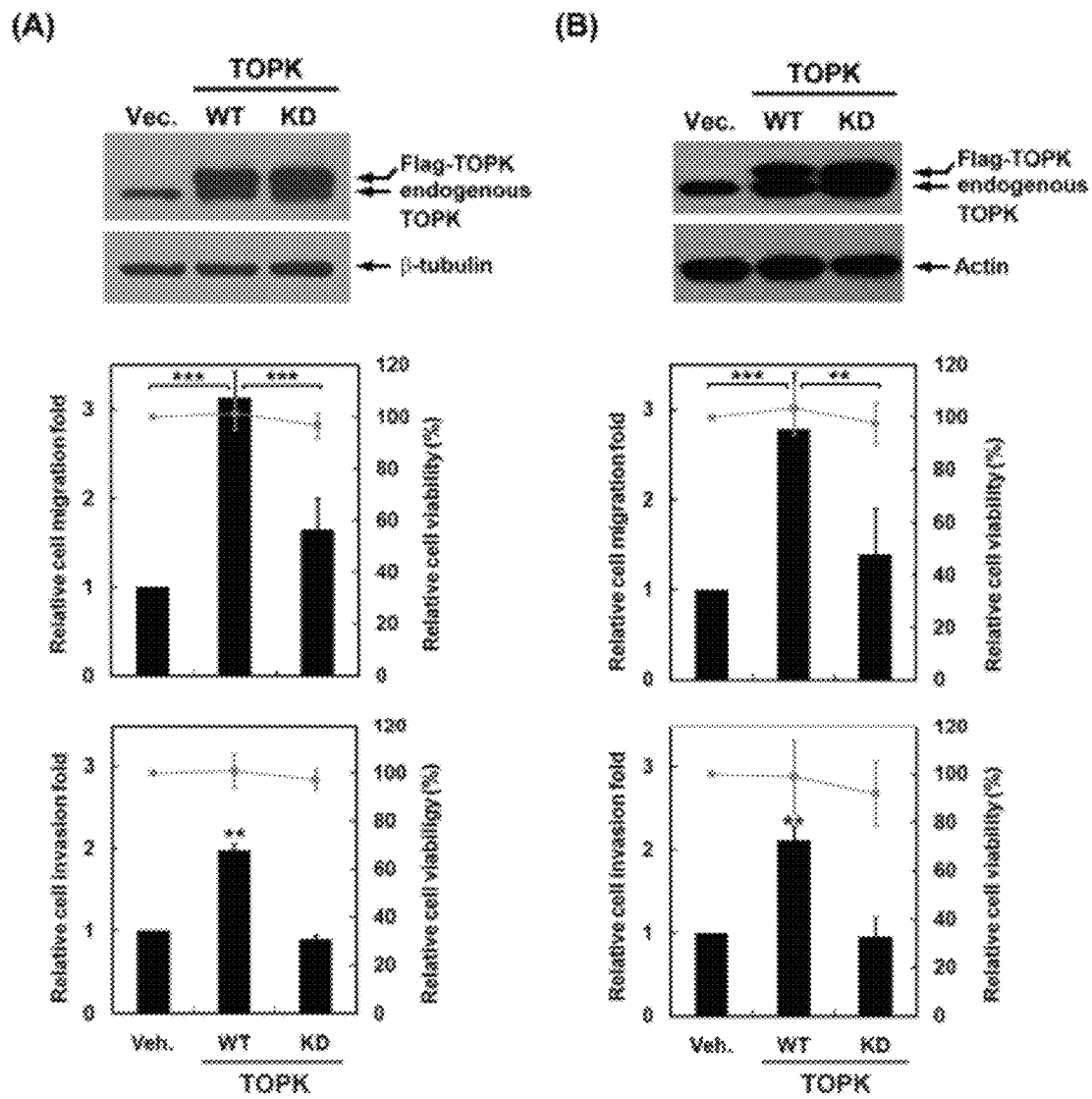
Figure 3:
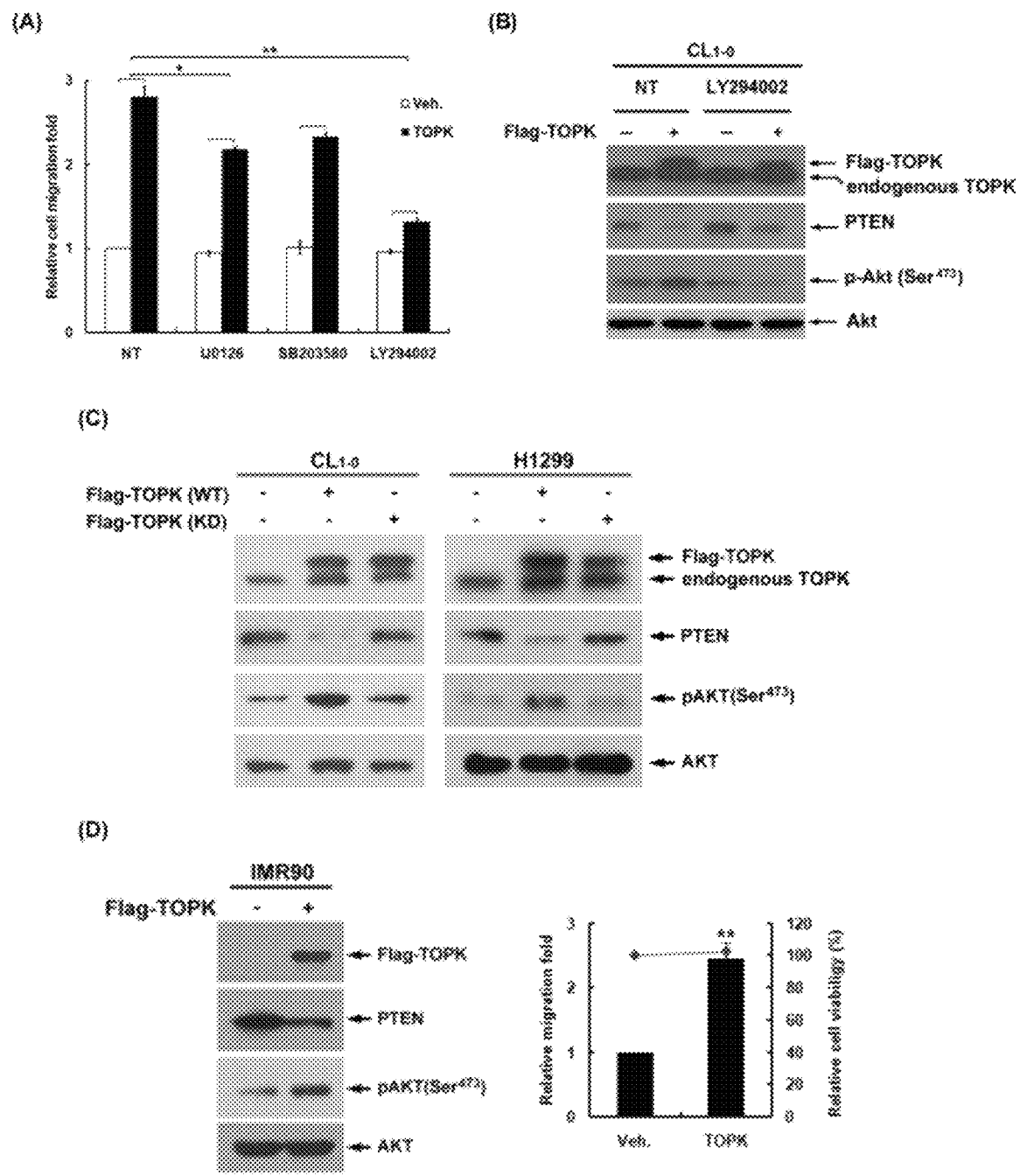
Figure 4:
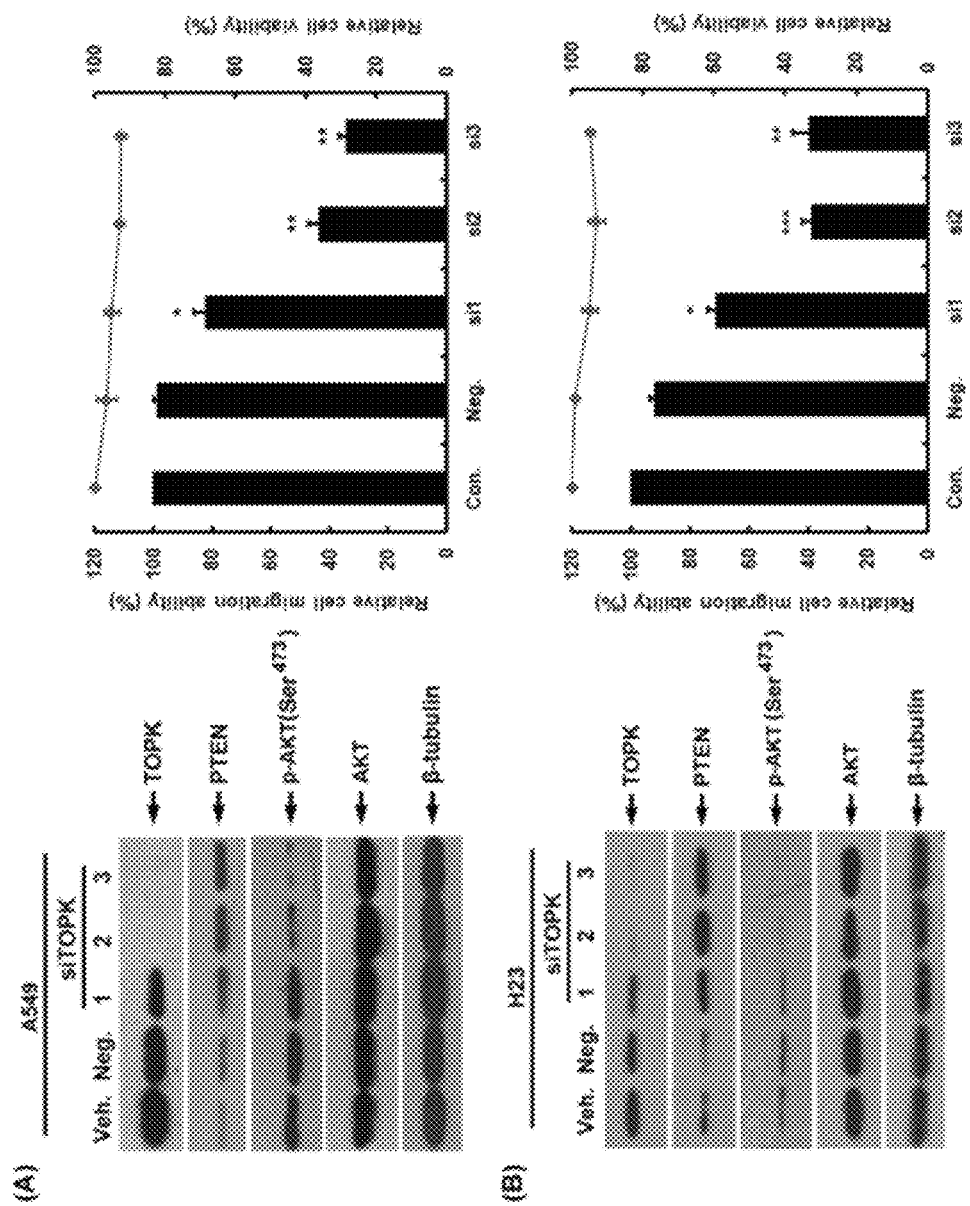
Figure 5:
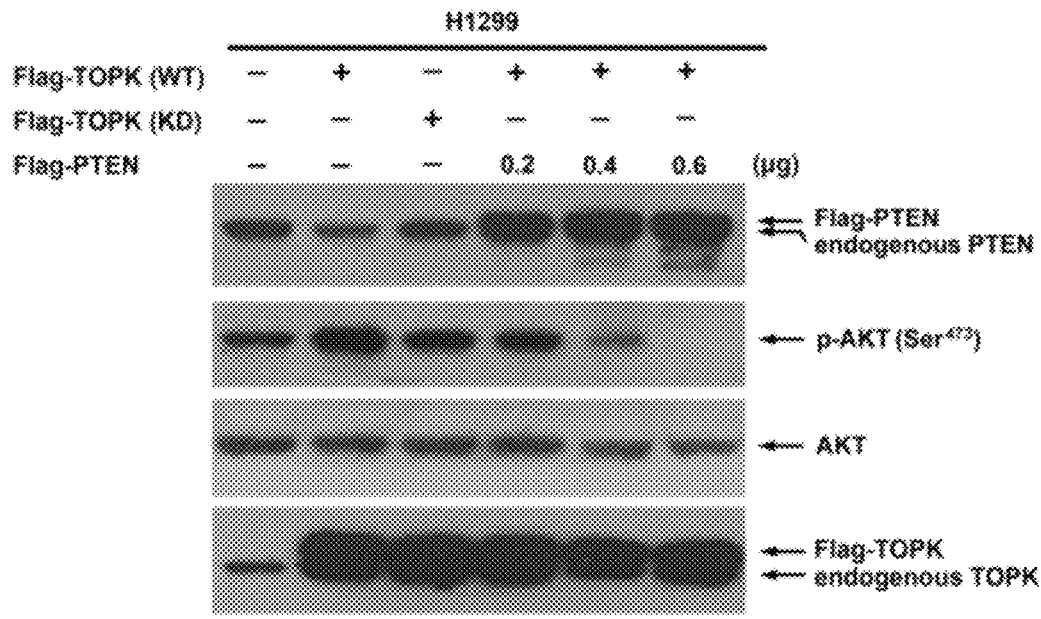
Figure 5:
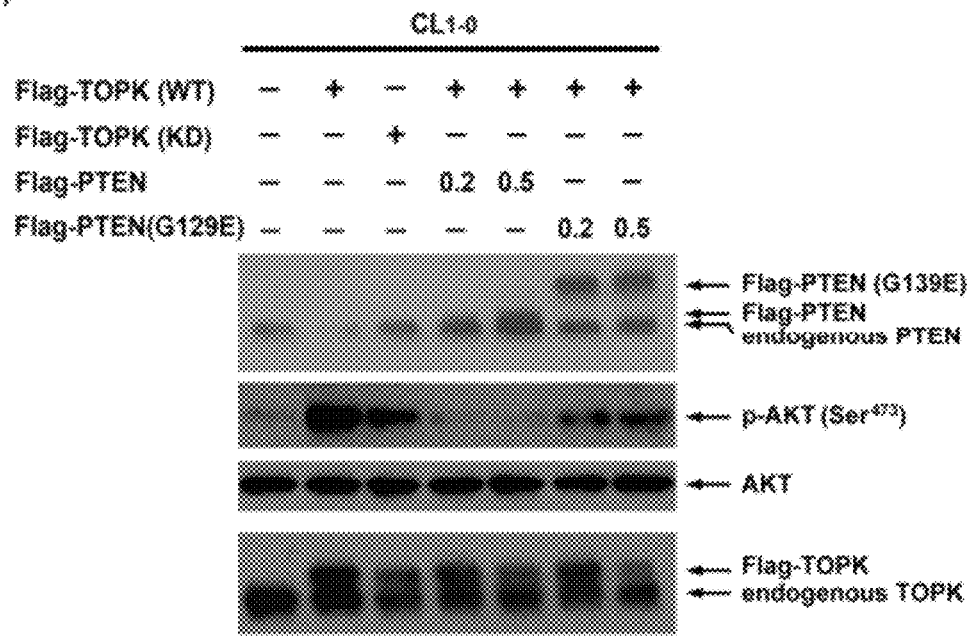
Figure 6:
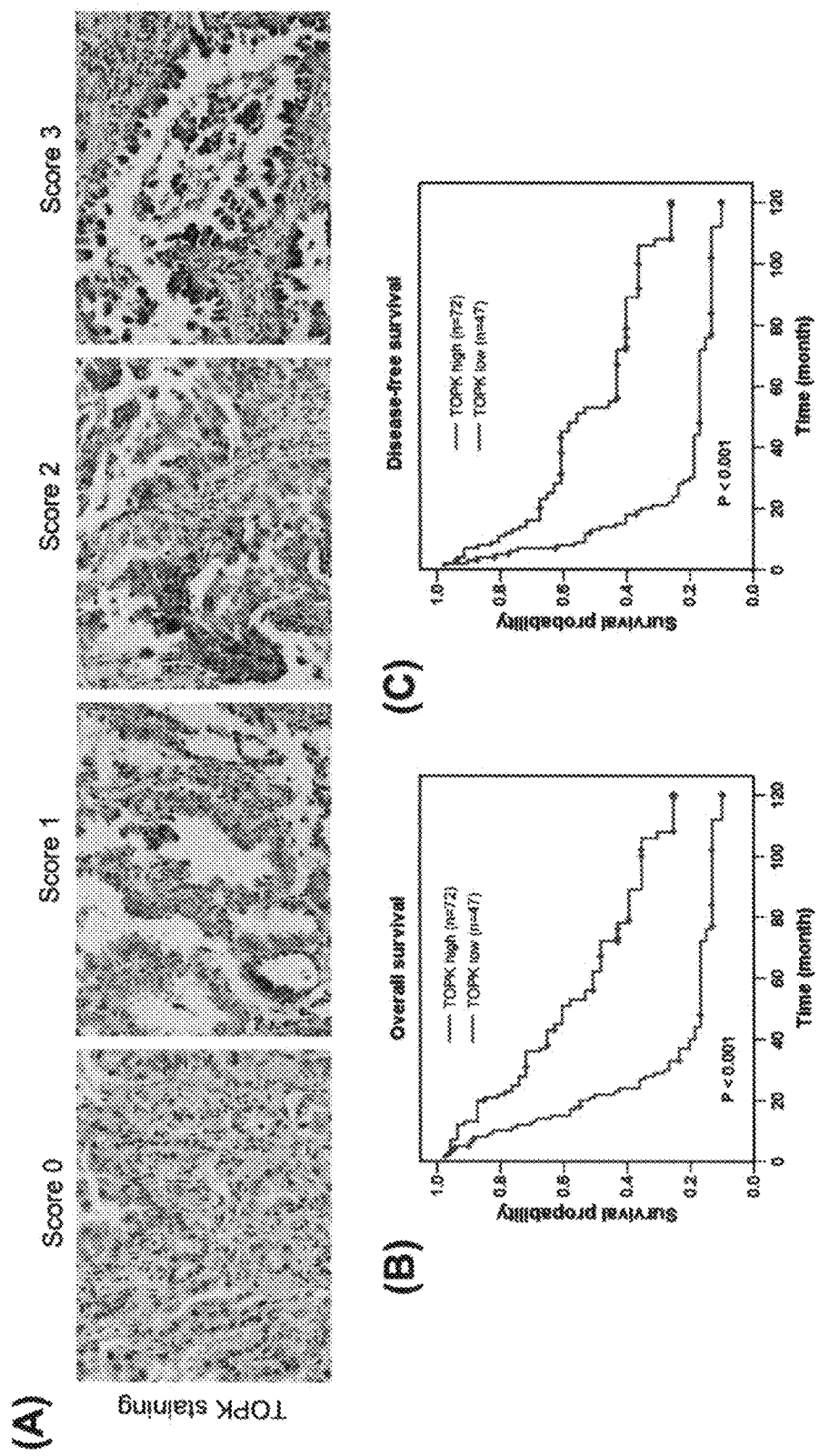
Figure 7:
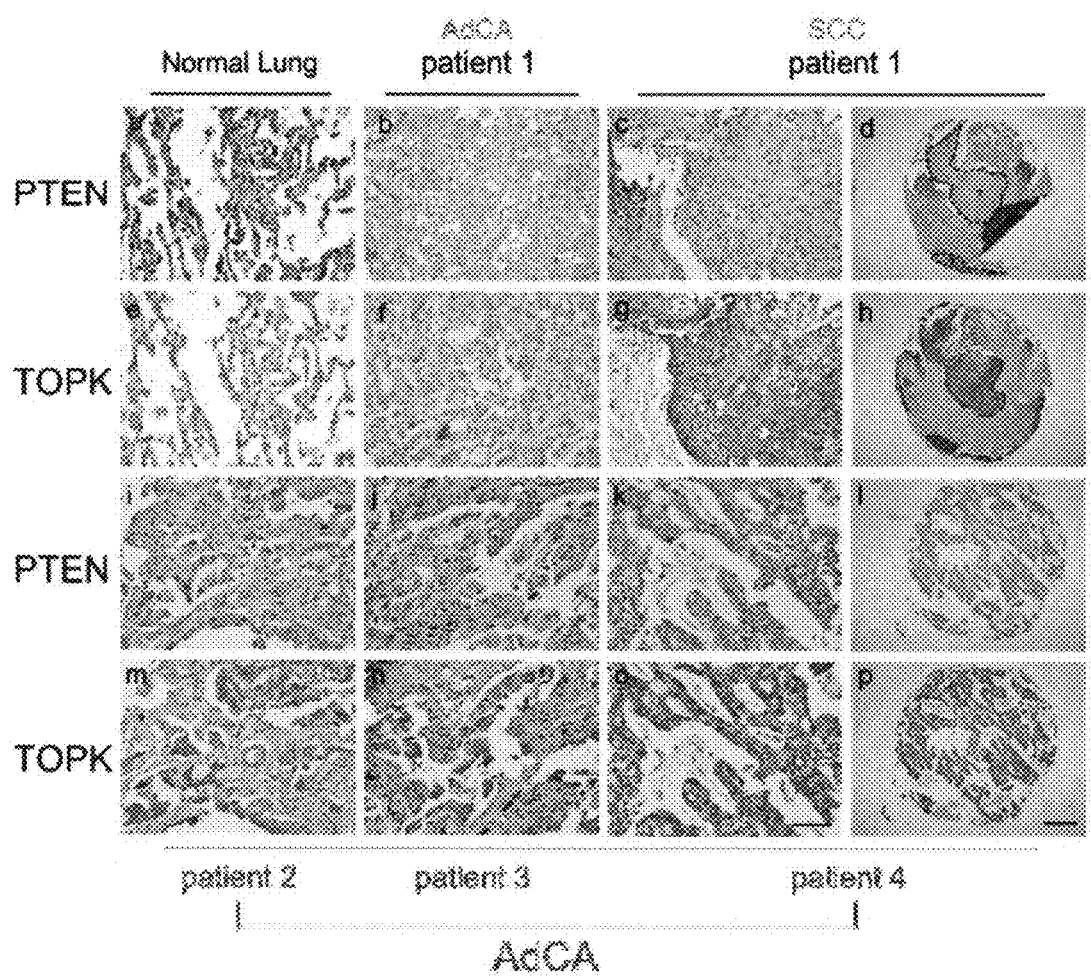
Figure 8:
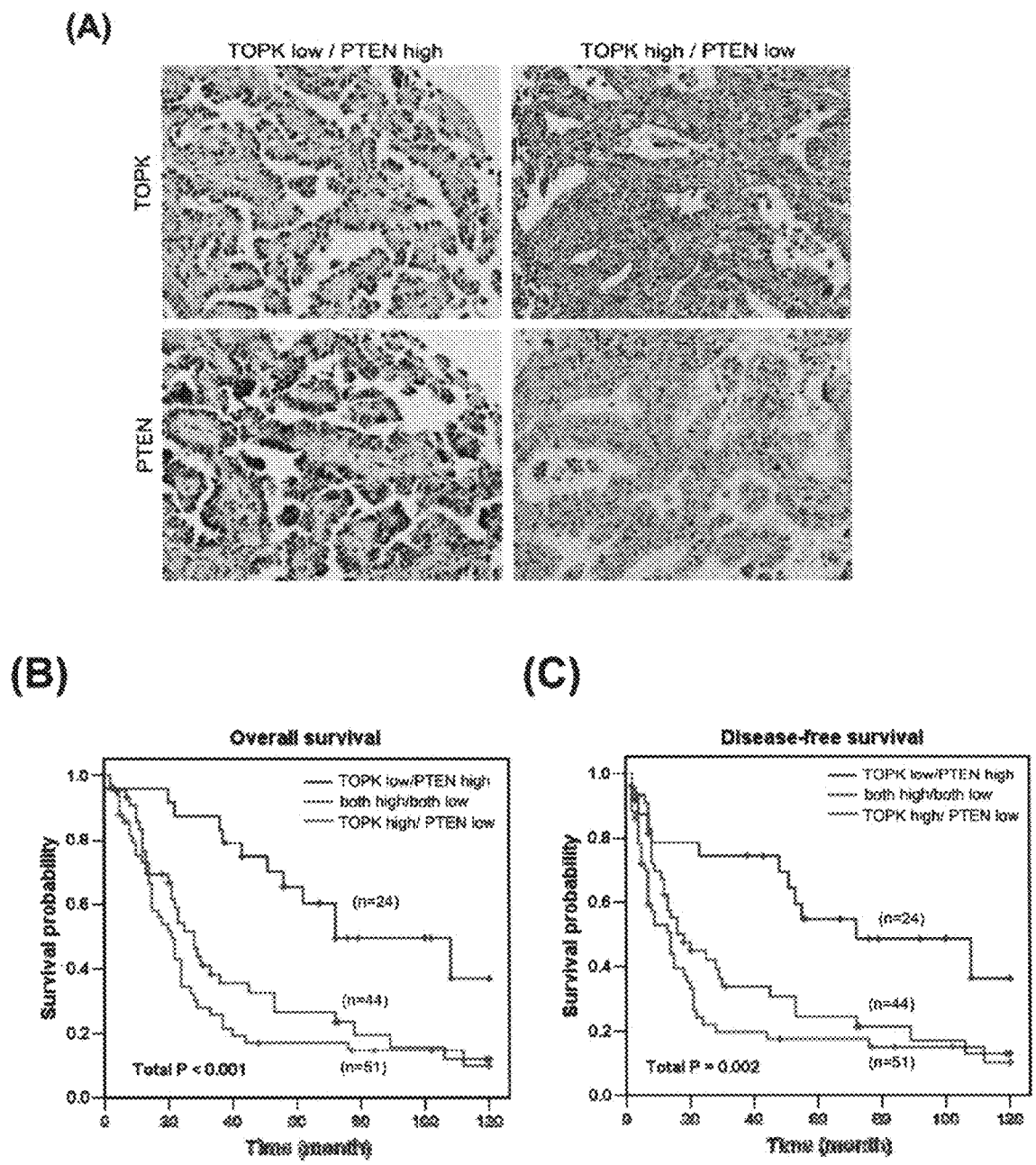
Figure 9:
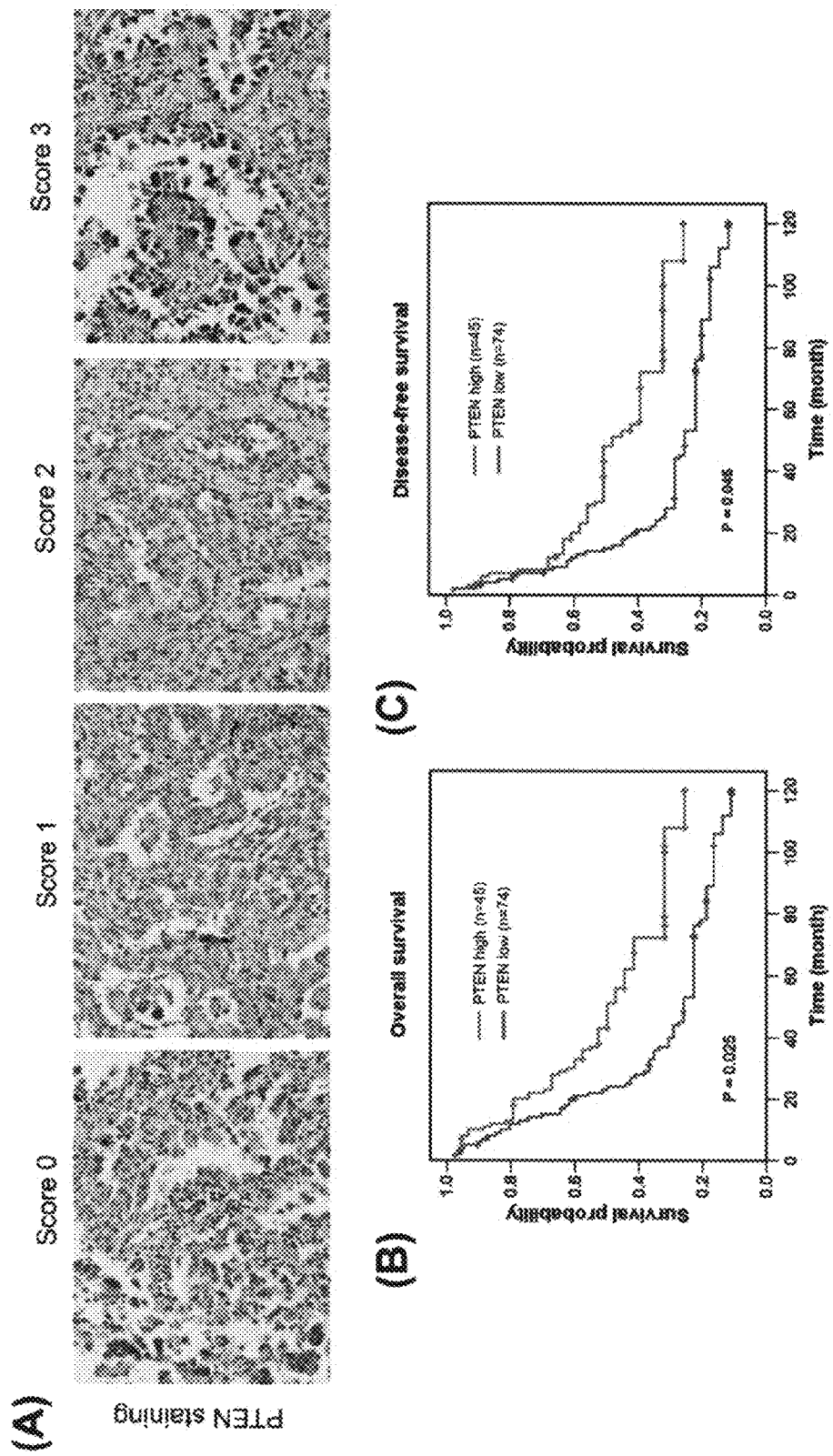
Figure 10:
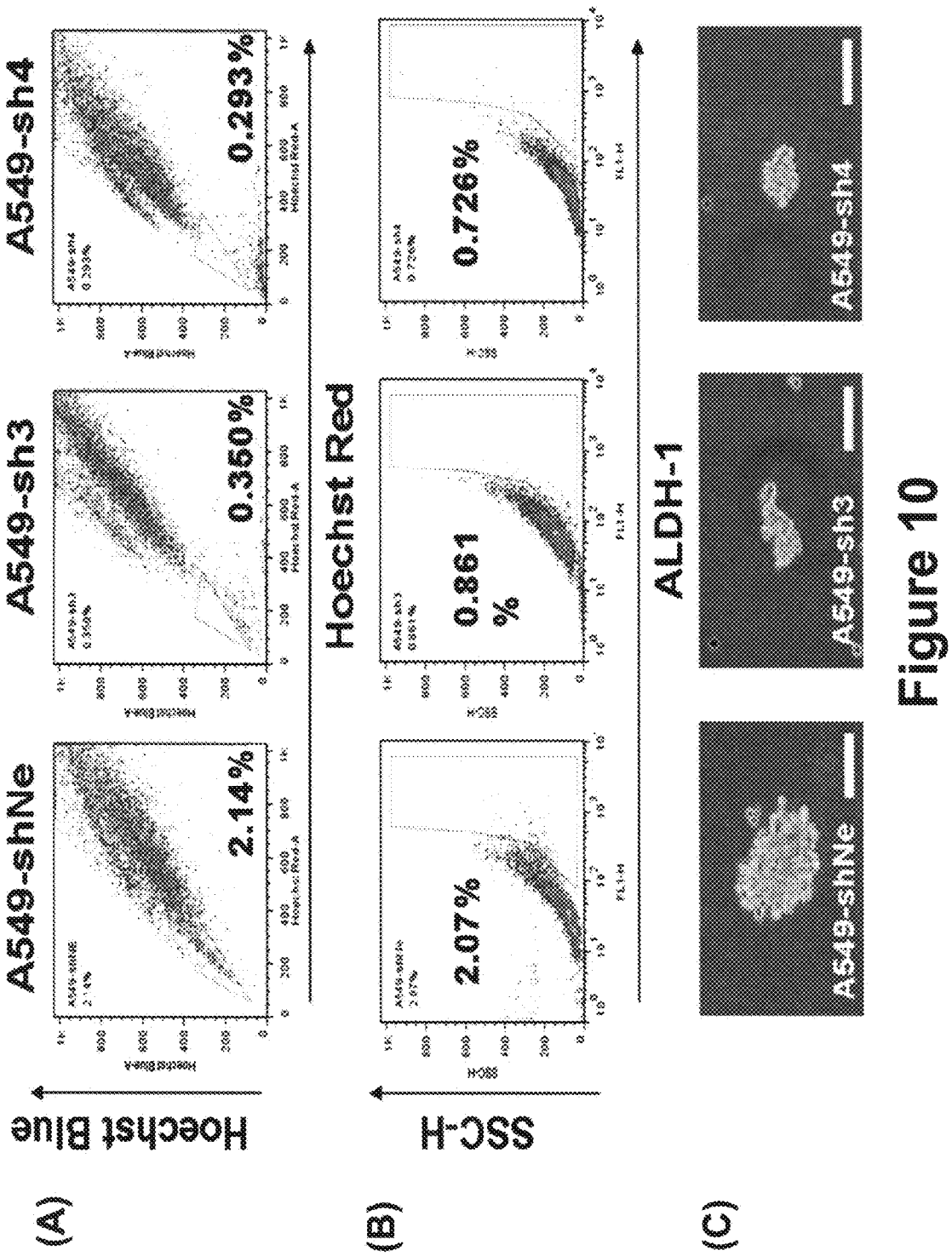

FIG. 1 shows that the TOPK expression is up-regulated in lung adenocarcinomas; wherein (A) the microarray expression patterns of TOPK (219148_at), EGFR (201984_s_at) and AURKA (208079_s_at) from 27 lung adenocarcinoma patients were normalized against the expression patterns on HG-U133A chips (left panel); and a different set of 25 lung adenocarcinoma patient specimens was subjected to microarray analysis using HG-U133 plus 2.0 chips (right panel); the boxplot shows the data distribution as a grouping classification and indicates that there are statistically significant differences ($p<0.0001$, left panel; $p<0.001$, right panel) between the tumor tissues and the adjacent non-tumor tissues; (B) the microarray expression patterns of TOPK were compared among 30 benign tumors and 220 metastatic tumors (first two panels) and are shown in a boxplot ($p<0.001$); the differential expression of TOPK in 5 commercially available brain tissues and 6 brain metastases derived from lung adenocarcinomas is also illustrated ($p=0.043$); (C) the mRNA levels of TOPK in samples from 24 lung adenocarcinoma patients, which are the same as those in (A, left panel), were determined by Q-RT-PCR. The results were normalized to the level of DDX5 mRNA in each paired sample and plotted in a boxplot ($p=0.004$); (D) BEAS-2B, BES-6, IMR90 cells and a panel of lung cancer cell lines were harvested and subjected to immunoblot analysis for detection of TOPK expression. β-tubulin staining was included as a loading control. (IMR90: human lung fibroblast cell line; A549, H23, $CL_{1-0}$ and $CL_{1-5}$: human lung adenocarcinoma cell line; H1299: human lung epithelial carcinoma cell line);

FIG. 2 provides the results of the overexpression of TOPK, which increased the migration and invasion of lung cancer cell lines; wherein (A) $CL_{1-0}$ or (B) H1299 cells were transiently transfected with (vehicle; Veh.) or pCMV2-Flag-TOPK (WT) or pCMV2-Flag-TOPK (KD) plasmids. Twenty-two hours post-transfection, one portion of the cells was harvested for detection of TOPK and β-tubulin or actin by immunoblotting (lower panels); the other portions of cells were seeded onto Matrigel-coated or uncoated transwell inserts or 96 well plate and incubated for another 24 hrs; the cell growth was quantified by an MTT assay; the numbers of migrated (middle panels) and invaded (lower panels) cells were then counted and expressed as relative migration or fold invasion as compared to vehicle control (n=3~6) (*$P<0.05$, $P<0.01$, *$P<0.001$);

FIG. 3 shows that TOPK modulated PTEN/PI3K/AKT signaling in lung cancer cells and lung fibroblasts; wherein (A) $CL_{1-0}$ cells were transiently transfected with a vector control or pCMV2-Flag-TOPK plasmid, twenty-two hours after transfection, cells were seeded onto transwell inserts and incubated for another 24 hrs; prior to counting the migrated cells, three different pharmacological inhibitors, U0126, SB203580 and LY294002 (10 µM), were added into separate transwell inserts, which were then incubated for another 2 hrs; and then, the number of migrated cells was counted and expressed as cell migration relative to vector transfected and untreated cells (Veh./NT); (B) one portion of cells from (A) was harvest for detection of phospho-AKT ($Ser^{473}$), AKT, PTEN and TOPK by immunoblotting. $CL_{1-0}$ (C, left), H1299 (C, right), and IMR90 (D) cells were transiently transfected with a vector control or pCMV2-Flag-TOPK (WT) or pCMV2-Flag-TOPK (KD) plasmid; twenty-two hours after transfection, a fraction of the cells was harvested for immunoblotting as indicated in (B); the migration and cell viability of TOPK-overexpressing IMR90 cells was also evaluated as described previously (D, right panel) (*$P<0.05$, $P<0.01$, *$P<0.001$);

FIG. 4 provides the results of knockdown of TOPK enhancing the expression of PTEN and decreases the activation of AKT in lung cancer cell lines; wherein A549 (A) and H23 (B) cells were transfected without (vehicle; Veh.) or with a scrambled siRNA (Neg.) or one of three TOPK-specific siRNAs (siTOPK); forty-eight hours after transfection, a fraction of the cells was harvested for detection of TOPK, PTEN, phospho-AKT ($Ser^{473}$), AKT and β-tubulin by immunoblotting; a portion of the cells was seeded onto a transwell insert and incubated for another 24 hrs. The number of migrated cells was then counted (A and B, right panels) (*$P<0.05$, $P<0.01$, *$P<0.001$);

FIG. 5 provides the overexpression of PTEN reversing TOPK-mediated AKT activation; wherein H1299 (A) and $CL_{1-0}$ (B) cells were transiently transfected with a vector control, pFlag-CMV2-TOPK (WT), pFlag-CMV2-TOPK (KD) and pFlag-CMV2-PTEN or pFlag-CMV2-PTEN (G129E) plasmid in different combination as indicated. Twenty-two hours after transfection, cells were harvested for detection of phospho-AKT ($Ser^{473}$), AKT, PTEN and TOPK by immunoblotting;

FIG. 6 provides the overexpression of TOPK being a marker of poor prognosis in lung cancer; wherein (A) shows TOPK protein expression in representative lung cancer specimen. TOPK levels were quantified according to the cytoplasmic staining intensity of TOPK. The results were classified into two groups according to the intensity of staining: in the low-expression group, either no staining was present (staining intensity score=0) or positive staining was detected in less than 10% of the cells (staining intensity score=1); in the high-expression group, positive immunostaining was present in 10% to 30% (staining intensity score=2) or more than 30% of the cells (staining intensity score=3). Kaplan-Meier plot of overall survival (B) and disease-free survival (C) in 119 lung cancer patients, stratified by TOPK expression;

FIG. 7 provides the IHC staining of endogenous PTEN and TOPK protein expression in paraffin sections of normal lung tissue and lung cancer samples; wherein endogenous PTEN expression was detected by immunohistochemistry in normal lung (a), adenocarcinomas (b, i, j, k, l) and squamous cell carcinomas (c and d); it showed the strong cytoplasmic expression of PTEN protein found in normal lung and adenocarcinoma samples, and the weak or absent PTEN protein expression in adenocarcinoma (AdCA) samples 2 to 4 and the squamous cell carcinoma (SCC) samples; endogenous TOPK expression was detected by immunohistochemistry in adenocarcinoma (m, n, o, p), and squamous cell carcinoma (g and h) samples; it indicated the strong cytoplasmic TOPK staining in adenocarcinoma samples 2 to 4 and SCC sample (g); the yellow arrowheads indicated strong membrane expression of TOPK in SCC (g) and AdCA (m, n, p); and the weak to absent TOPK expression in normal lung (e) and adenocarcinoma sample 1 (f); the scale bar in (o) represents 50 µm; and the scale bar in (p) represents 200 µm;

FIG. 8 provides an inverse correlation between TOPK and PTEN expression being a potential prognostic factor in lung cancer; wherein (A) shows immunohistochemical staining of TOPK and PTEN in serial sections; it showed the inverse correlation between the level of TOPK and that of PTEN. Overall (B) and disease-free (C) survival of 119 patients with respect to high TOPK and low PTEN expression;

FIG. 9 provides the results of the down-regulation o PTEN being a marker for poor prognosis in lung cancer; wherein (A) shows PTEN protein expression in a representative lung cancer specimen; PTEN levels were quantified according to the cytoplasmic staining intensity of PTEN; Kaplan-Meier plot of overall (B) and disease-free (C) survival in 119 lung cancer patients, stratified by PTEN expression;

FIG. 10 provides the results of knockdown of TOPK decreasing cancer stem cells characteristics in A549 cells; wherein (A) is the result of Hoechst dye exclusion assay showing that the percentage of SP cells was dramatically decreased in TOPK shRNA stably transfected A549 cells; (B) is the result of ALDH activity assay showing that knockdown of TOPK reduced $ALDH^+$ cell population; and (C) is the result of primary tumor sphere assay, a measurement of CSCs of self-renewal capacity, demonstrating the decreased tumor sphere formation in TOPK knockdown cells. The photograph shown here is a representative image of two experiments (Original magnification, x 200).

Figure 11:
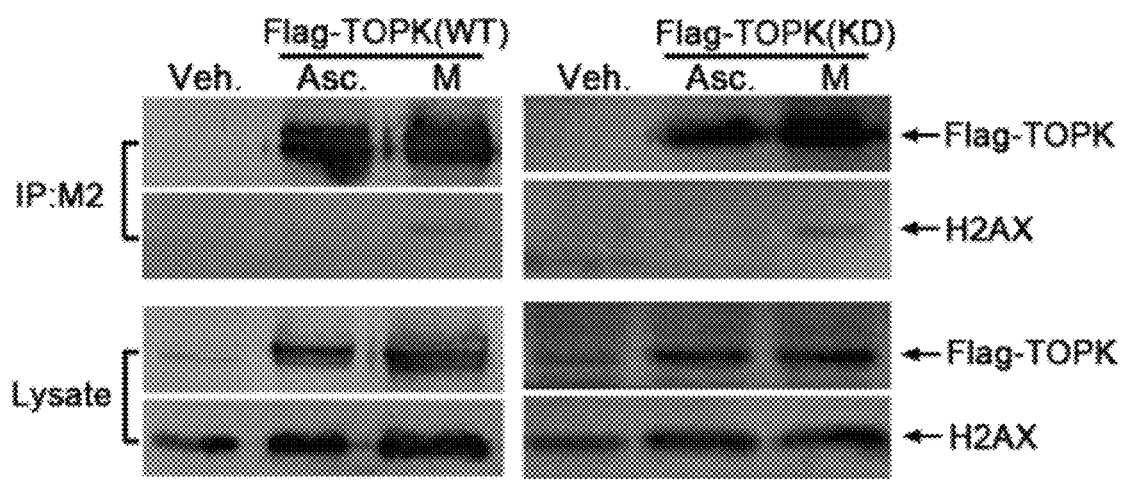

FIG. 11 demonstrates that TOPK interacts with H2AX in M phase, wherein H1299 cells were transiently transfected with vector control (Veh.) and pCMV2-Flag-TOPK (WT) and (KD) plasmids, respectively. Twenty-four hr post-transfection, one portion of Flag-TOPK expression cells was treated with nocodazole (75 ng/ml) for 24 hrs, which served as M phase arrested cells, whereas the other portion of cells did not incubate with nocodazole and served as asynchronized cells (Asc.). Cells were then harvested for immunoprecipitation by M2 beads and followed by immunoblotting.

Figure 12:
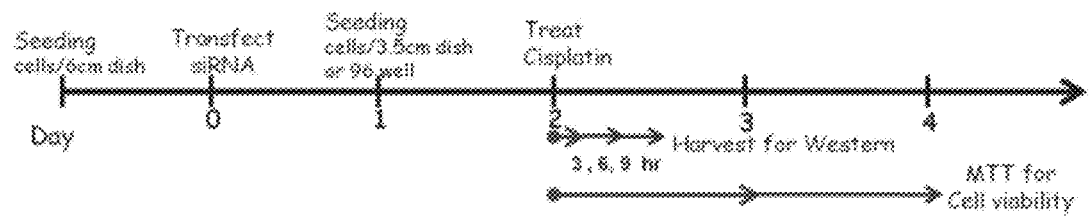
Figure 12:
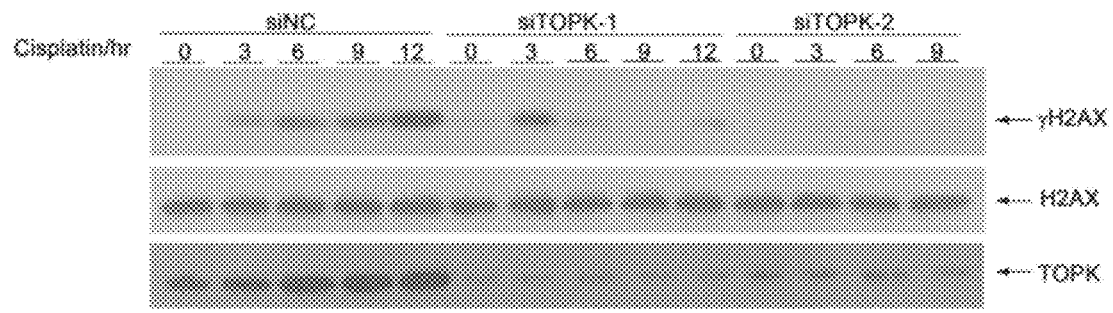
Figure 12:
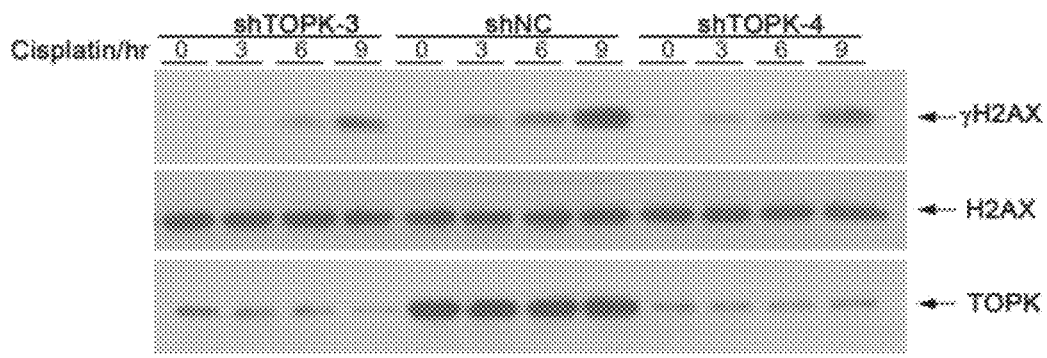

FIG. 12 provides results of knockdown of TOPK significantly decreasing cisplatin-induced γ-H2AX, wherein (A) is schematic depiction of detection of cisplatin-induced H2AX phosphorylation in TOPK siRNA and shRNA transfected A549 cells; A549 cells transiently transfected with scramble control (siNC), siTOPK-1 (SEQ ID NO:1), and siTOPK-2 (SEQ ID NO:2) (B), or A549-Luc cells stably transfected with shNC, shTOPK-3 (SEQ ID NO:3), and shTOPK-4 (SEQ ID NO:4) (C) were treated with cisplatin (35 µM) for the indicated time period. Cells were harvested for detecting the expression of phospho-H2AX (γ-H2AX), H2AX and TOPK by immunoblotting.

Figure 13:
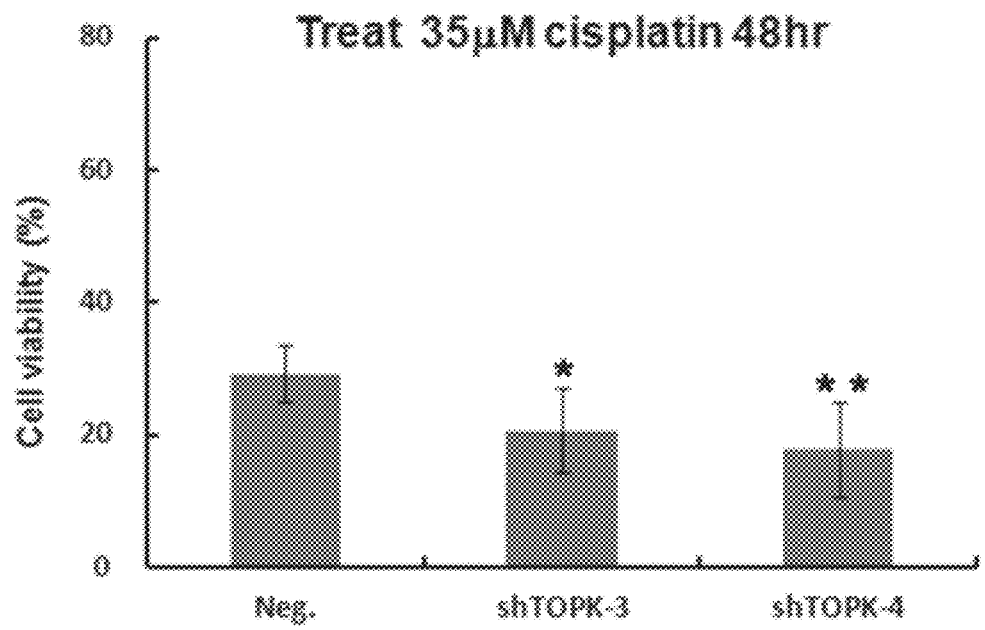

FIG. 13 provides the results of knockdown of TOPK sensitizing cisplatin-induced cell death, wherein A549-Luc cells stably transfected with shNC as control, and shTOPK-3 (SEQ ID NO:3), and shTOPK-4 (SEQ ID NO:4) respectively were treated with cisplatin (35 µM); after 48 hr, MTT assays were performed to examine the cell viability (n=5, * $P<0.05$, ** $P<0.01$).

Figure 14:
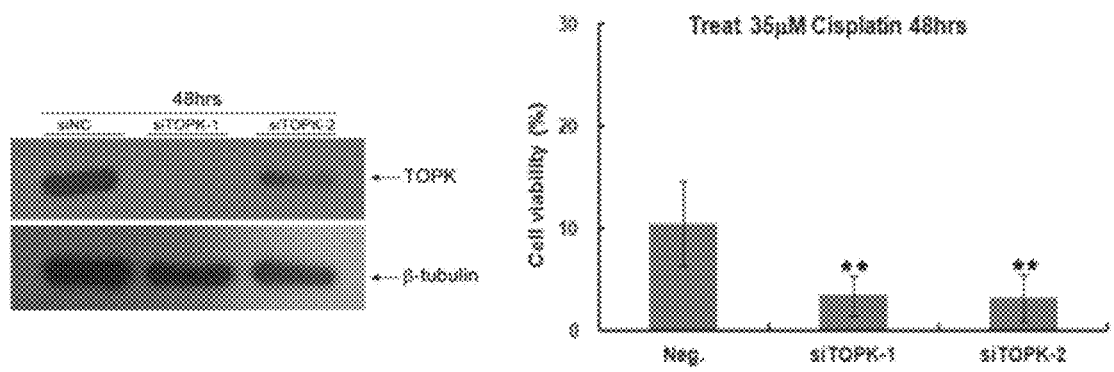

FIG. 14 shows that knockdown of TOPK promotes cisplatin-induced cell death in CL152 cells. CL152 cells transiently transfected with scramble control (siNC), siTOPK-1 (SEQ ID NO: 1), and siTOPK-2 (SEQ ID NO: 2) respectively were treated with cisplatin (35 µM). After 48 hr, MTT assays were performed to examine the cell viability (n=3, ** $P<0.01$).

Figure 15:
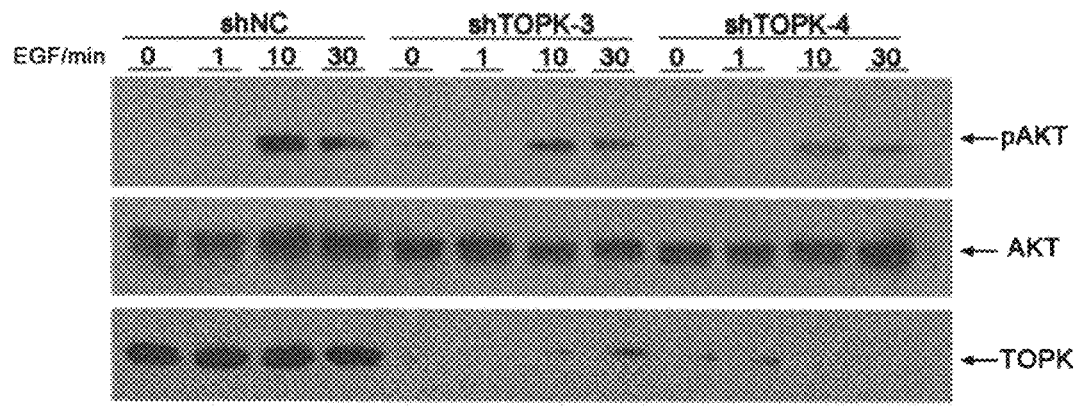

FIG. 15 provides the results of knockdown of TOPK decreasing EGF-induced AKT phosphorylation in A549-Luc cells. shNC, shTOPK-3 (SEQ ID NO: 3), and shTOPK-4 (SEQ ID NO: 4) stably transfected A549-Luc cells were serum deprived for 24 hrs. EGF (20 ng/ml) was added to stimulate cells for 0~30 min as indicated. Then, cells were harvested for detecting the expression of pAKT, AKT and TOPK by immunoblotting.

Figure 16:
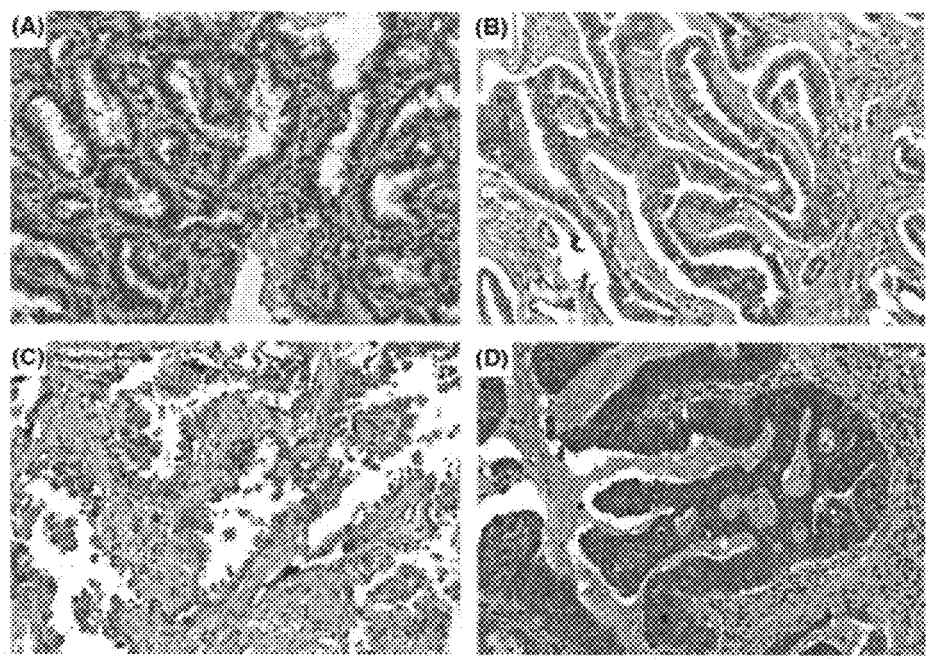
Figure 17:
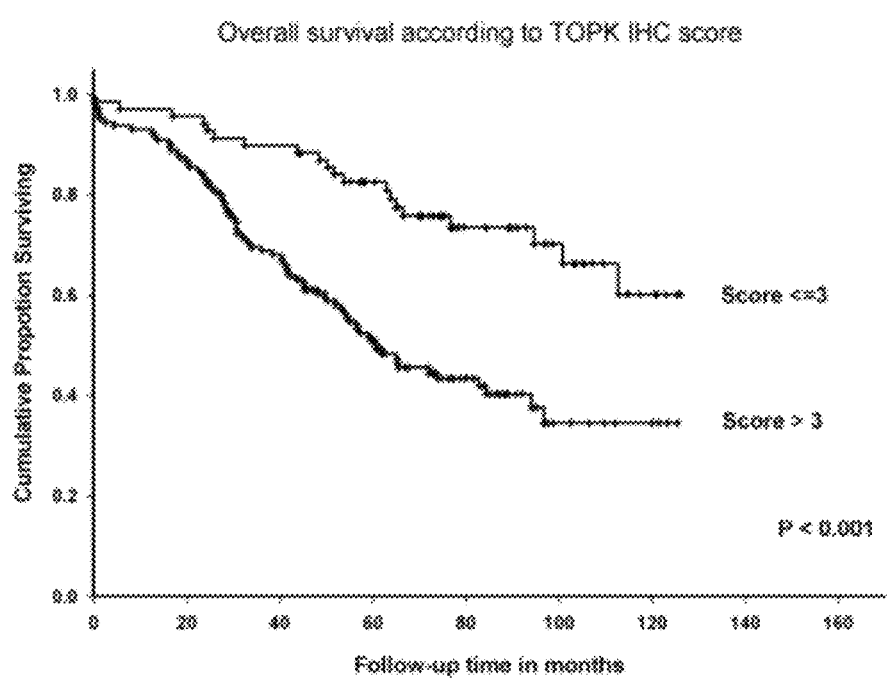
Figure 18:
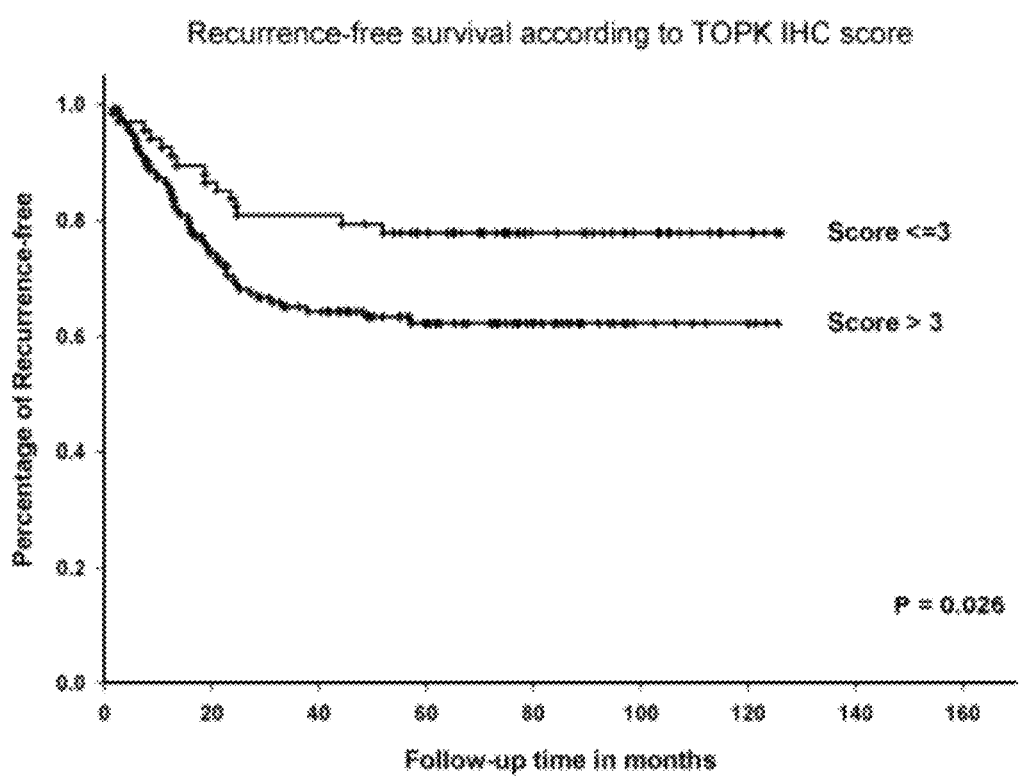

FIG. 16 provides the results of TOPK expression in stage I lung adenocarcinoma; wherein the intensity of immunoreactivity was recorded as 0 (negative) (A), 1 (weakly positive) (B), 2 (moderately positive) (C), and 3 (strongly positive) (D);

FIG. 17 provides the results of the overall patient survival according to TOPK IHC score; wherein the patients with high TOPK IHC score (>3) had poorer survival compared with those with low TOPK IHC score (<=3) ($p<0.001$); and FIG. 18 shows the recurrence-free survival according to TOPK IHC score; wherein the patients with high TOPK IHC score (>3) had poorer recurrence-free survival compared with those with low TOPK IHC score (<=3) ($p=0.026$).

DETAILED DESCRIPTION OF THE INVENTION

The term "T-lymphokine-activated killer cell-originated protein kinase (TOPK)," or "PDZ-binding kinase (PBK)," as used herein refers to a 322 amino acid MAPKK-like serine/threonine protein kinase.

In the invention, it is unexpectedly found that T-lymphocyte-activated killer cell-Originated Protein Kinase (TOPK) can be used a biomarker for identifying the subgroup of early-stage lung adenocarcinoma patients in early-stage non-small cell lung cancer (NSCLC), which is helpful for the design of clinical trials for adjuvant therapy. As found in the invention that TOPK is a potential therapeutic target in lung cancer that promotes cell migration by modulating a PI3K/PTEN/AKT-dependent signaling pathway. Since tumor recurrence is the most common cause of disease failure after surgical resection in early-stage lung adenocarcinoma, the overexpression of TOPK may predetermine the metastatic capability of tumors and can serve as a significant prognostic predictor of shortened overall survival and time to recurrence.

Accordingly, the invention provides a method for identifying the subgroup of early-stage lung adenocarcinoma patients in an early-stage NSCLC patient, comprising collecting a tissue sample from the patient, determining the level of TOPK expressed in the tissue sample, and identifying the subgroup of determining early-stage lung adenocarcinoma patients based on the TOPK expression, wherein the overall survival of the patient is worse if the overexpression of TOPK in the patient's tissue sample is found.

Furthermore, the invention provides a method for designing a clinical trial for the treatment of lung adenocarcinoma in early-stage NSCLC patients, comprising collecting a tissue samples from the patients, determining the TOPK expression of the tissue samples, identifying the subgroup of determining early-stage lung adenocarcinoma patients based on the TOPK expression, and sub-grouping the patients with the levels of survival in terms of the TOPK expression in the patients' tissue samples.

On the other hand, the present invention provides a method for evaluating the prognostic value in a patient in the resected stage I adenocarcinoma comprising collecting a tissue sample from the patient, determining the level of TOPK expressed in the tissue sample, and identifying the prognostic value of the patient based on the level of the TOPK expression, wherein the prognostic value of the patient is worse if the overexpression of TOPK in the patient's tissue sample is found.

In addition, it was confirmed in Examples 10 and 12 that the knockdown of TOPK could decrease cancer stem cells characteristics and sensitize cisplatin-induced cell death in A549 cells. Accordingly, the present invention provides a method for treating a cancer comprising administering a subject in need thereof a TOPK inhibitor at a therapeutically efficient amount to decrease cancer stem cells characteristics and sensitize cisplatin-induced cancer cell death.

In one embodiment of the invention, the cancer is lung cancer, particularly non-small cell lung cancer (NSCLC).

The term "TOPK inhibitor" as used herein refers to a molecule, compound, or substance that is capable of substantially inhibiting or decreasing the expression or activity of TOPK.

In one embodiment of the invention, the TOPK inhibitor may be a nucleic acid molecule such as a short (or small) interfering RNA (siRNA) or a short (or small) hairpin RNA (shRNA). The term "short (or small) interfering RNA" or "siRNA" as used herein refers to a double-stranded RNA molecule, having 20-25 nucleotides in length, that plays a role in the RNA interference (RNAi) pathway, where it interferes with the expression of a specific gene. The term "short (or small) hairpin RNA" or "shRNA" as used herein refers to a sequence of RNA that makes a tight hairpin turn that can be used to silence gene expression via RNA interference.

In another embodiment of the invention, the TOPK may be a compound selected from the group consisting of Thioridazine, Prochlorperazine, Skimmianine, Emetine, DL-thiorphan, Bisacodyl, Astemizole, Pyrvinium, Tanespimycin, Perphenazine, Trifluoperazine, Chlorpormazine, isoniazid, tacrolimus, and Fisetin, which are identified as potential inhibitors for TOPK by using gene signature from TOPK siRNA to query the Connectivity Map (CMap).[88]

According to the invention, the TOPK inhibitor is an siRNAs or an shRNA, which is capable of inhibiting or decreasing the expression of TOPK. In the examples of the invention, the siRNA is siTOPK-1 having a first strand as set forth in SEQ ID NO: 1 or siTOPK-2 having a first strand as set forth in SEQ ID NO: 2. In other examples of the invention, the shRNA is shTOPK-3 having a sequence as set forth in SEQ ID NO:3 or shTOPK-4 having a sequence as set forth in SEQ ID NO:4. Both of the siRNA and shRNA can be delivered to the cells in any way known or commonly used in the art.

The present invention will now be described more specifically with reference to the following embodiments, which are provided for the purpose of demonstration rather than limitation.

EXAMPLES

I. Clinical Trial Data and Q-RT-PCR Analysis

Materials/Subjects and Methods

Clinical Samples for Microarray and Q-RT-PCR Analysis

Two lung adenocarcinoma microarray datasets were used in this study. First, a total of 66 samples from our previous study were used for microarray analysis via HG-U133A chip. These include pair-matched samples from 27 patients who underwent surgery for lung cancer and several lung cancer cell lines, e.g., $CL_{1-0}$ and $CL_{1-5}$. Second, 50 additional samples, corresponding to 25 pair-matched surgical samples from lung cancer patients, were subjected to microarray analysis via HG-U133 plus 2.0 chip. These two datasets have been deposited in NCBI's Gene Expression Omnibus (GEO) and are accessible through GEO series accession numbers GSE7670 and GSE27262. The study protocol was approved by the ethics committee at Taipei Veterans General Hospital. All patients gave informed consents and signed the consent form individually (VGHIRB No.: 95-06-21A). None of the patients had previously received any neoadjuvant treatment, e.g., chemotherapy, before surgery. Study samples, including tumor and adjacent normal tissues as confirmed by pathologists, were obtained during diagnostic biopsy, and adjacent normal tissues were derived from a neighboring site outside of the tumor. Both tumor and adjacent normal tissues were snap-frozen in liquid nitrogen, and RNA samples were isolated for microarray analysis and subsequent Q-RT-PCR studies. Tumor histology and stages were classified according to the World Health Organization classification and the international staging system for lung cancer.[47,3] The mRNA expression level of TOPK in 18 pair-matched tumor and adjacent normal samples from lung cancer patients was validated using Q-RT-PCR, which was performed with a TaqMan probe (ABI). Assays were performed in triplicate using Applied Biosystems Model 7700 instruments. Data are represented as mean±s.d. To analyze the distribution of tumor and adjacent normal samples, we performed the Wilcoxon signed rank test between two groups for statistical analysis.

Immunohistochemical Staining

The tissues used were from Kaohsiung Medical University Hospital. All clinical samples were obtained, with informed consent and institutional review board approval, from patients undergoing tumor resection or surgical procedures at Kaohsiung Medical University. Patient information, including gender, age and histopathological diagnoses, was collected. The surgical specimens had been fixed in formalin and embedded in paraffin before they were archived. We used the archived specimens for immunohistochemical staining. Follow-up of patients was carried out for up to 200 months. A four-point staining intensity scoring system was devised for determining the relative expression of TOPK in cancer specimens; the staining intensity score ranged from 0 (no expression) to 3 (maximal expression). All of the immunohistochemical staining results were reviewed and scored independently by two pathologists. The antibodies included anti-human TOPK (1:100, Cell Signaling) and PTEN (1:50, Dako). Immunodetection was performed with a HRP-DAB detection kit (Vector Laboratories). Cox proportional hazards regression was used to test the prognostic significance of factors in univariate and multivariate models. Spearman's rank correlations were determined for comparison of TOPK and PTEN immunohistochemical staining. All statistical tests were two-sided, and $p<0.05$ was considered significant.

Cells, Reagents, Migration and Invasion Assays

All cell culture related reagents were purchased from Invitrogen. Human lung cancer cell lines A549, H23 and H1299, as well as IMR90 cells are purchased from American Type Culture Collection. Human lung adenocarcinoma cell lines, $CL_{1-0}$ and $CL_{1-5}$, were kind gifts from Dr. Pan-Chyr Yang. All cells were cultured in appropriate medium, e.g., RPMI 1640 for A549, $CL_{1-0}$ and $CL_{1-5}$; DMEM for IMR90, H1299 and H23. Each medium were supplemented with 10% fetal bovine serum, 2 mM of L-glutamine and 1% penicillin/streptomycin. Transfection of cells was done using lipofetamine (Invitrogen) according to the manufacturer's instructions. To knockdown intrinsic expression of TOPK, three siRNA sequences directed against TOPK (si-TOPK1: 5'-GCAGC-CAUAAUUUUAAAAGdTdT-3', si-TOPK2: 5'-CCCUGAGGCUUGUUACAUUdTdT-3', si-TOPK3: 5'-GCUCUGGAAACAGAUGUCUdTdT-3') were purchased from Applied Biosystems. A scrambled siRNA duplex was also obtained as a negative control. At 24 or 48 hr post-transfection, cells were harvested and subjected to a migration or proliferation assay and the protein level of TOPK was determined by western blotting as described previously (Chen et al 2009a). Pharmacological inhibitors used (LY294002, U0126, and SB203580) were from Cell Signaling. Primary antibodies (dilutions) used include: anti-TOPK (1:1000, BD Biosciences), anti-Flag M2 (1:3000; Sigma), anti-phospho-AKT (1:1000, Cell Signaling), anti-AKT (1:1000, Cell Signaling), anti-PTEN (1:1000, Cell Signaling), anti-β-tubulin (1: 3000, Santa Cruz Biotechnology) and anti-HA (1: 3000, Upstate).

Cloning and Mutagenesis

To construct the TOPK expression plasmids, the sequence of TOPK cDNA was PCR amplified from the MCG clone using Pfu Turbo DNA polymerase (Stratagene). The primer sets used were 5'-ATACA<u>CGGTCCG</u>ATGGAAGGGATCAGTAATTTC-3' and 5'-GATGA<u>CGGACCG</u>CTAGACATCTGTTTCCAGAGC-3' (underlines indicate recognition sites of the restriction enzyme) for wild-type TOPK. The PCR products were inserted into the CPO1 sites of pCMV-2-FLAG or pcDNA3.1-HA expression vector respectively. We also generated a kinase-dead (KD) mutant, in which Lys64 and Lys65 were substituted with Ala (K64-65A).[17]

Results

1. Identification of TOPK as an Up-Regulated and Metastasis-Related Protein Kinase in Lung Adenocarcinoma Via the Integration of Gene Expression Datasets To rapidly prioritize targets for lung cancer therapy, particularly poorly characterized protein kinases involved in metastasis, we set up a bioinformatics platform integrating four transcriptome datasets for the identification of such genes. As a result of our bioinformatics survey, we focused on the poorly characterized gene TOPK. First, we used a training microarray dataset, namely samples from 27 patients with lung adenocarcinoma confirmed by histopathology, which were subjected to Affymetrix microarray profiling using HG-U133A.[55] Of many differentially expressed transcripts between the adjacent normal area and the tumor examined by Wilcoxon signed rank test ($p<0.01$) and tested using the Benjamini and Hochberg false discovery rate correlation ($p<0.01$), TOPK expression was up-regulated, as shown by boxplot (FIG. 1A, left). Two well-known oncogenic protein kinases, EGFR and AURKA, were shown to be overexpressed in the same datasets (FIG. 1A, left), consistent with the idea that microarray profiling can represent an unprecedented platform for discovery novel regulators involved in the carcinogenesis of, for example, lung cancer. Second, to validate this observation, we conducted an independent microarray profiling 25 pair-matched, stage 1 lung adenocarcinoma patient specimens by using a new Affymetrix microarray (HG-U133 plus 2.0) chip and the same statistical analyses. Again, TOPK expression was up-regulated in the tumor compared to the adjacent normal area (FIG. 1A, right).

Third, to provide additional information in our in silico screening, we created two sets of metastasis signatures. Public accessible microarray data (downloaded from GEO) were used to acquire different microarray datasets, which were normalized by Quantile Normalization using R to set up a potential metastatic biomarker identification platform. We compared 225 secondary metastatic tumors (including 20 tumor metastases to the lymph node and 200 metastatic tumors) and 30 benign tumors to obtain sets of potential promoters of metastasis, as described previously.[47] TOPK exhibits differential expression patterns, as shown by boxplot (FIG. 1B, left). Finally, because lung cancer often metastasizes to the brain after gefitinib treatment,[52] we compared 6 commercially available normal brains and 5 specimens of lung adenocarcinoma metastasis to brain. Differentially expressed genes were considered to have the potential to participate in lung adenocarcinoma metastasis, and TOPK was one of them (FIG. 1B, right). The combination of these four distinct microarray datasets identifies TOPK as an overexpressed and metastasis-related protein kinase in lung adenocarcinoma. These data raise the possibility that up-regulation of TOPK might lead to some of the abnormalities found in human lung adenocarcinoma.

2. Elevated TOPK Expression in Lung Adenocarcinomas and Invasive Lung Cancer Cell Lines To clarify the underlying molecular mechanisms of TOPK in lung cancer progression, we first validated the gene expression profiling data for TOPK. Quantitative real-time PCR was performed on 24 pair-matched lung adenocarcinoma tumors and adjacent non-tumor samples. Overexpression of TOPK was observed in 20 out of 24 lung patient tumors, showing a higher signal after normalization to DDX5, a novel internal control for lung adenocarcinoma,[55] for equal template loading. The average expression level of TOPK in lung adenocarcinoma was ~5 fold higher than that in adjacent non-tumor lung tissue samples, as analyzed by boxplot (FIG. 1C). Next, we examined and compared the protein expression levels of TOPK in the human lung fibroblast line IMR90 and a panel of lung cancer cell lines. As shown in FIG. 1D, TOPK protein was markedly expressed in the lung cancer cell lines and undetectable in IMR90 cells. Moreover, the protein level of TOPK was higher in the highly invasive $CL_{1-5}$ as compared to the less invasive $CL_{1-0}$ cells.

3. Overexpression of TOPK Enhances Cell Migration and Invasion in Lung Cancer Cell Lines Because the expression of TOPK correlates with the invasiveness of lung cancer cells, it is likely that the expression of TOPK plays a role in cancer metastasis. We therefore investigated whether overexpression of TOPK could affect cell migration or invasion in NSCLC cell lines with low levels of endogenous TOPK, such as $CL_{1-0}$ and H1299 cells. We transiently transfected vector control and Flag-tagged TOPK expression plasmids into $CL_{1-0}$ and H1299 cells, respectively, and tested the effect of TOPK on cell migration, invasion and cell proliferation. As expected, exogenous Flag-tagged TOPK was overexpressed in $CL_{1-0}$ and H1299 cells, which resulted in 3.1 fold ($CL_{1-0}$) and 2.8 fold (H1299) increase in cellular migration and a ~2 fold ($CL_{1-0}$ and H1299) increase in cellular invasion as compared to the control cells (FIGS. 2A and B). The observed migration- and invasion-promoting abilities of TOPK were largely depended on its kinase activity, because overexpression of a catalytically inactive TOPK (TOPK-KD) had no significant effect on cell migration or invasion. In addition, though TOPK is reported to be overexpressed in highly proliferative cells (Simons-Evelyn et al 2001), ectopically overexpression of TOPK did not significantly affect cell proliferation at 24 hr, indicating TOPK could enhance the migratory and invasive ability of lung cancer cells without promoting proliferation.

4. PI3K/AKT-Dependent Signaling is Critical for TOPK-Induced Cell Migration

Tumor cells possess a broad spectrum of migration and invasion mechanisms that are associated with enhanced metastasis.[46] To explore which signal transduction pathways might participate in TOPK-mediated cell migration in lung cancer cells, we investigated three well-defined signaling pathways, namely the MEK/ERK, p38 and PI3K/AKT pathways, using specific pharmacological inhibitors. The increase in cell migration stimulated ectopic expression of TOPK in $CL_{1-0}$ cells was strongly decreased by treatment with LY294002 and inhibited to a smaller extent by U0126 and SB203580 (FIG. 3A). Moreover, elevated AKT-$Ser^{473}$ phosphorylation was observed in TOPK-WT-expressing $CL_{1-0}$ cells compared with vehicle and TOPK-KD-expressing cells. Similar results were obtained in H1299 cells (FIG. 3C). Together, these data indicate that the PI3K/AKT pathway is involved in TOPK-induced cell migration.

5. Inverse Correlation of AKT Phosphorylation and PTEN Level in TOPK-Overexpressing Cells PTEN is a lipid phosphatase that acts as a tumor suppressor by negatively controlling the PI3K/AKT signaling pathway. Inactivation of PTEN often results in increased AKT activity in many types of tumors, including lung adenocarcinoma.[64,68] The ectopic expression of PTEN in various tumor cell lines exerts inhibitory effects on several known biological actions of PI3K signaling pathway, e.g., migration.[40] In addressing how TOPK modulates the PI3K/AKT pathway, we noticed that the protein expression level of PTEN was decreased in TOPK-WT-overexpressing cells as compared to vehicle and TOPK-KD transfected cells (FIG. 3B-C). To provide additional evidence to support this notion, ectopic expression of TOPK in the human lung fibroblast line IMR90, which does not contain detectable endogenous TOPK, was also evaluated. Despite low transfection efficiency in IMR90, overexpression of TOPK resulted in down-regulation of PTEN, up-regulation of AKT-$Ser^{473}$ phosphorylation and enhanced cell migration (FIG. 3D), consistent with our other observations.

6. siRNA-Mediated Depletion of Endogenous TOPK Suppresses Lung Cancer Cell Migration and PI3K/AKT Signaling To further confirm that TOPK affects cell migration by modulating the PI3K/PTEN/AKT signaling pathway, we next examined if TOPK-specific siRNAs could affect cell migration and activation of endogenous AKT in A549 cells. We transfected three chemically synthesized siRNAs specific for TOPK (si-TOPK1~3) and a scrambled control siRNA (Neg.) into A549 cells and analyzed the expression of TOPK at 48 hr post-transfection. The data showed different degrees of reduction in the TOPK protein in TOPK siRNA-transfected cells, which correlated with decreases in cell migration (FIG. 4A). In accordance with the previous results, the reduction of migration in TOPK-depleted cells did not result from differences in cell proliferation rates, as shown in a cell proliferation assay. In addition, the data indicated that AKT-$Ser^{473}$ phosphorylation was greatly reduced in TOPK-depleted cells as compared to that seen in vehicle-treated or scrambled control cells and that this reduction occurred in parallel with an increase in the PTEN protein level (FIG. 4A, left panel). Similar results were also observed in H23 cells (FIG. 4B). Together, these results strengthen of the evidence for TOPK modulation of the PI3K/PTEN/AKT signaling pathway.

7. TOPK Induces PI3K/AKT-Dependent Cell Migration by Relieving PTEN-Mediated Negative Regulation To determine whether TOPK mediated AKT-dependent cell mortality by regulating the PTEN protein level, we first examined whether co-treating cells with LY294002, a PI3K inhibitor, could affect the TOPK-induced decrease in PTEN. As shown in FIG. 3B, the presence of LY294002 significantly inhibited the phosphorylation of AKT but had no effect on the TOPK-induced reduction of PTEN. Moreover, when PTEN was ectopically expressed, TOPK-induced phosphorylation of AKT-Ser$^{473}$ was blocked in a dose-dependent manner (FIG. 5A). Because PTEN-G129E, which lacks lipid phosphatase activity, had a smaller effect on TOPK-mediated AKT activation, the data suggest the lipid phosphatase activity of PTEN is crucial for negative regulating AKT activity in lung cancer cells and TOPK that can promote AKT-dependent cell migration by down-regulating the protein level of PTEN (FIG. 5B).

8. TOPK is a Marker for Poor Prognosis in Lung Cancer

To provide an independent validation, the prognostic value of TOPK expression was determined by assessing its immunoreactivity using 119 human lung cancer specimens, which were not the same as those examined in our microarray studies (FIG. 1), with known clinical follow-up records. High tumor TOPK expression levels (scores of 2 and 3) were more strongly associated with patients with reduced overall and disease-free survival relative to low TOPK expression level (scores of 0 and 1) (FIG. 6). The relationships between the levels of TOPK expression and the clinicopathologic characteristics of lung cancer are summarized in Table 1.

TABLE 1

Relationships between TOPK expression and clinicopathological factors in 119 lung cancer patients.

| Characteristics | TOPK expression Low (0, 1) (n = 47) | TOPK expression High (2, 3) (n = 72) | P value |
|---|---|---|---|
| Age | | | 0.64 |
| Years (mean ± SD) | 62.0 ± 9.5 | 60.0 ± 10.3 | |
| Sex | | | 0.43 |
| Male | 27 | 36 | |
| Female | 20 | 36 | |
| Smoking status | | | 0.65 |
| No | 30 | 43 | |
| Yes | 17 | 29 | |
| Histological type | | | |
| Adenocarcinoma | 31 | 40 | 0.08 |
| Squamous cell carcinoma | 9 | 29 | |
| Large cell carcinoma | 7 | 3 | |
| Stage[#] | | | <0.001* |
| I + II | 32 | 18 | |
| III + IV | 15 | 54 | |
| Tumor status[#] | | | 0.07 |
| T1-2 | 41 | 53 | |
| T3-4 | 6 | 19 | |
| Lymph node status[#] | | | 0.01* |
| N0 | 25 | 18 | |
| N1-3 | 22 | 43 | |
| Distal metastasis status[#] | | | 0.37 |
| M0 | 35 | 48 | |
| M1 | 12 | 24 | |
| Recurrence status | | | 0.08 |
| No | 30 | 34 | |
| Yes | 17 | 38 | |

*A p value <0.05 was considered statistically significant (Student's t test for continuous variables and Pearson chi-square test for categorical variables).
SD represents standard deviation.
[#]The tumor stage, tumor, lymph node, and distal metastasis status were classified according to the international system for staging lung cancer.

Overexpression of TOPK in lung cancer is associated with advanced stage (p<0.001) and lymph node metastasis (p=0.01). The univariate survival analysis demonstrated that the TOPK score and the pathologic assessment of the primary tumor (T), lymph nodes (N) and metastases (M) had an impact on overall and disease-free survivals (Table 2).

TABLE 2

Cox univariate and multivariate regression analysis of TNM prognostic factors and TOPK expression with overall and disease-free survival in 119 lung cancer patients.

| Variables | Comparison | HR (95% CI) | P-value |
|---|---|---|---|
| Cox univariate analysis (OS) | | | |
| T | T1-T2; T3-T4 | 1.832 (1.159-2.894) | 0.01* |
| N | N0; N1-N3 | 2.037 (1.282-3.237) | 0.003* |
| M | M0; M1 | 2.628 (1.673-4.129) | <0.001* |
| TOPK | Low (0, 1); High (2, 3) | 2.501 (1.585-3.946) | <0.001* |
| Cox multivariate analysis (OS) | | | |
| T | T1-T2; T3-T4 | 1.007 (0.613-1.653) | 0.978 |
| N | N0; N1-N3 | 1.451 (0.894-2.357) | 0.132 |
| M | M0; M1 | 2.446 (1.520-3.935) | <0.001* |
| TOPK | Low (0, 1); High (2, 3) | 2.323 (1.430-3.775) | 0.001* |
| Cox univariate analysis (DFS) | | | |
| T | T1-T2; T3-T4 | 1.944 (1.229-3.076) | 0.004* |
| N | N0; N1-N3 | 2.079 (1.305-3.314) | 0.002* |
| M | M0; M1 | 2.319 (1.479-3.637) | <0.001* |
| TOPK | Low (0, 1); High (2, 3) | 2.281 (1.446-3.599) | <0.001* |
| Cox multivariate analysis (DFS) | | | |
| T | T1-T2; T3-T4 | 1.177 (0.723-1.917) | 0.512 |
| N | N0; N1-N3 | 1.532 (0.941-2.495) | 0.086 |
| M | M0; M1 | 2.072 (1.300-3.305) | 0.002 |
| TOPK | Low (0, 1); High (2, 3) | 2.021 (1.252-3.262) | 0.004 |

NOTE:
Cox proportional hazards regression was used to test the independent prognostic contribution of TOPK after accounting for other potentially important covariates.
Abbreviations:
OS, overall survival;
DFS, disease-free survival;
HR, hazard ratio;
CI, confidence interval.
*Two-sided Cox proportional hazards regression using normal approximation (p < 0.05 showing a statistical significance).

The multivariate analysis also showed that the TOPK score and M-status significantly affected the overall and disease-free survivals (see Table 2). Taken together, our data indicate that a high level of TOPK can be used as an independent prognostic factor in lung cancer.

9. TOPK Expression is Inversely Associated with PTEN Expression in Lung Cancer Patients To investigate the interplay between TOPK and PTEN in lung cancer patients, we performed IHC analysis of TOPK and PTEN in serial sections of lung cancer tissues. The representative IHC staining for TOPK and PTEN showed a trend towards inverse staining pattern in normal lung, lung adenocarcinoma and lung squamous cell carcinoma (FIG. 7). We next investigated the prognostic significance of PTEN by IHC analysis. FIG. 9 shows that a high PTEN expression level (scores of 2 and 3) correlated strongly with better overall and disease-free survival relative to low PTEN expression level (scores of 0 and 1). The relationships between PTEN expression and clinicopathological characteristics of lung cancer are summarized in Table 3-1. The multivariate analysis showed that the PTEN score (p=0.025), N-status (p=0.022) and M-status (p=0.001) significantly affected overall survival (Table 3-2). The PTEN score, however, strongly but non-significantly affected the disease-free survival (p=0.086) as assessed by multivariate analysis. We further investigated the degree of inverse correlation between TOPK and PTEN expression in serial sections of human lung cancer tissues. The IHC analysis of lung cancer specimens revealed an inverse correlation between TOPK and PTEN expression (FIG. 8A), with a correlation coefficient=−0.221 (p=0.016), as analyzed by Spearman's nonparametric correlation test (Table 3-3).

TABLE 3-1

Relationships between PTEN expression and clinicopathological factors in 119 lung cancer patients
PTEN expression

| Characteristics | Low (0, 1) (n = 74) | High (2, 3) (n = 45) | P value |
|---|---|---|---|
| Age | | | 0.42 |
| Years (mean ± SD) | 62.0 ± 9.4 | 60.0 ± 12.0 | |
| Sex | | | 0.29 |
| Male | 42 | 21 | |
| Female | 32 | 24 | |
| Smoking status | | | 0.03* |
| No | 39 | 33 | |
| Yes | 35 | 12 | |
| Histological type | | | |
| Adenocarcinoma | 46 | 25 | 0.06 |
| Squamous cell carcinoma | 25 | 14 | |
| Large cell carcinoma | 3 | 6 | |
| Stage# | | | 0.32 |
| I + II | 28 | 22 | |
| III + IV | 46 | 23 | |
| Tumor status | | | 0.11 |
| T1-2 | 49 | 36 | |
| T3-4 | 25 | 9 | |
| Lymph node status | | | 0.78 |
| N0 | 26 | 17 | |
| N1-3 | 48 | 28 | |
| Distal metastasis status | | | 0.81 |
| M0 | 51 | 32 | |
| M1 | 23 | 13 | |
| Recurrence status | | | 0.86 |
| No | 40 | 25 | |
| Yes | 34 | 20 | |

*A p value <0.05 was considered statistically significant (Student's t test for continuous variables and Pearson chi-square test for categorical variables).
SD represents standard deviation.
The tumor stage, tumor, lymph node, and distal metastasis status were classified according to the international system for staging lung cancer.

TABLE 3-2

Cox univariate and multivariate regression analysis of TNM prognostic factors and PTEN expression with overall and disease-free survival in 119 lung cancer patients

| Variables | Comparison | HR (95% CI) | P-value |
|---|---|---|---|
| Cox univariate analysis (OS) | | | |
| T | T1-T2; T3-T4 | 1.832 (1.159-2.894) | 0.01* |
| N | N0; N1-N3 | 2.037 (1.282-3.237) | 0.003* |
| M | M0; M1 | 2.628 (1.673-4.129) | <0.001* |
| PTEN | High (2, 3); Low (0, 1) | 1.658 (1.054-2.608) | 0.029* |
| Cox multivariate analysis (OS) | | | |
| T | T1-T2; T3-T4 | 1.224 (0.759-1.976) | 0.407 |
| N | N0; N1-N3 | 1.756 (1.086-2.839) | 0.022* |
| M | M0; M1 | 2.251 (1.408-3.598) | 0.001* |
| PTEN | High (2, 3); Low (0, 1) | 1.691 (1.068-2.677) | 0.025* |
| Cox univariate analysis (DFS) | | | |
| T | T1-T2; T3-T4 | 1.944 (1.229-3.076) | 0.004* |
| N | N0; N1-N3 | 2.079 (1.305-3.314) | 0.002* |
| M | M0; M1 | 2.319 (1.479-3.637) | <0.001* |
| PTEN | High (2, 3); Low (0, 1) | 1.522 (0.968-2.394) | 0.069 |
| Cox multivariate analysis (DFS) | | | |
| T | T1-T2; T3-T4 | 1.355 (0.838-2.194) | 0.216 |
| N | N0; N1-N3 | 1.756 (1.085-2.841) | 0.022* |
| M | M0; M1 | 1.937 (1.212-3.094) | 0.006* |
| PTEN | High (2, 3); Low (0, 1) | 1.492 (0.945-2.356) | 0.086 |

NOTE:
Cox proportional hazards regression was used to test the independent prognostic contribution of TOPK after accounting for other potentially important covariates.
Abbreviations:
HR, hazard ratio;
CI, confidence interval.
*Two-sided Cox proportional hazards regression using normal approximation. A p value <0.05 was considered statistically significant.

TABLE 3-3

Correlation between TOPK and PTEN levels in 119 lung cancer patients

| | PTEN | |
|---|---|---|
| TOPK | Low (0, 1) | High (2, 3) |
| Low (0, 1) | 23 | 24 |
| High (2, 3) | 51 | 21 |

Inverse correlation between TOPK and PTEN levels (tested by Spearman's nonparametric correlation test, correlation coefficient = −0.221, p = 0.016).

Moreover, high TOPK and low PTEN expression, when taken together, were correlated with poor overall (p<0.001) and disease-free survival (p=0.002), compared to patients with low TOPK and high PTEN expression (FIG. 8B-C).

The HR of overall and disease-free survival for TOPK is higher than that of lymph node status (N) and close to that of distal metastasis status (M) (see Table 2). The subgroup analysis using both TOPK and PTEN expression levels further showed that patients with high TOPK and low PTEN levels had a significantly poorer outcome in terms of overall and disease free survival compared to the group of patients with low TOPK/high PTEN levels. Moreover, the 5-year survival probability of the low TOPK/high PTEN group is more than three times greater than that of patients with high TOPK/low PTEN expression (see FIG. 8 and FIG. 9). These results indicate that TOPK expression is clinically associated with PTEN expression and can be used as an independent prognostic factor to predict the treatment outcomes of patients with lung cancer.

In view of the above results on the prognostic value of TOPK in patients with resected stage I lung adenocarcinoma, older age and TOPK overexpression were significant independent prognostic indicators for overall survival in multivariate analysis. TOPK overexpression was also a significant prognostic factor for recurrence-free survival in multivariate analysis. TOPK overexpression was associated with significantly worse overall and recurrence-free survivals in this study.

10. Knockdown of TOP Decreases the Characteristics of Cancer Stem Cells

TOPK has been implicated as a proliferating neural progenitor-specific MAPK kinase, which plays an important role in neural progenitor proliferation and self-renewal. In addition, TOPK has recently been found in the list of cancer stem cell-based signature.[83] Cancer stem-like cell (CSC), a subpopulation of limited number, with the ability to self-renew and undergo asymmetrical divisions, giving rise to a differentiated progeny that represents most of the tumor populations. Since CSCs are generally metastatic and chemoresistant, these features are very likely to contribute to the poor response of locally advanced lung cancer.

Followings are three means to isolate lung CSCs. First, the side population assay relies on the ability of ABC transporters expressed in stem cell population to efflux the fluorescent Hoechst 33342 dye. Hoechst 33342 dye excluding cells, referred to as side population cells (SP cells), have been described in a variety of tumor types as being enriched in stem-like properties. In human lung cancer as few as 1,000 isolated SP cells from lung cancer cell lines produce roust xenografts in mice, whereas non-SP cells failed to generate tumors with similar numbers of SP cells.[84] Second, using flow cytometry to sort tumor cells for the extracellular portions of surface stem cell markers is another common strategy for isolating CSCs. CD133 is a cell surface glycoprotein that consists of five transmembrane domains and two large glycosylated extracellular loops, which recently have been reported as a marker for lung CSCs.[85] Similar to other cancer stem cell studies, some of lung tumor derived CD 133$^+$ cells could be expanded in vitro as floating tumor spheres cultured in defined serum free media. These CD133$^+$ cells enriched spheres were refractory to chemotherapy, suggesting that putative CD133$^+$ lung CSCs are resistant to conventional chemotherapy. Finally, another method for identifying stem cell populations is based on aldehyde dehydrogenase (ALDH) activity. ALDH enzymes are a family of intracellular enzymes that participate in cellular detoxification, differentiation and drug resistance through the oxidation of cellular aldehydes. ALDH$^+$ cells isolated from NCI-H358 and NCI-H125 lung cancer cell lines are enriched in tumorigenic, CD133$^+$ cancer cells. In addition, high levels of ALDH1 protein expression correlates with poor patient prognosis, which consistent with the hypothesis that ALDH$^+$ lung tumor cells are enriched in lung cancer stem cells.[86]

To evaluate the role of TOPK in cancer stem cells, we have used previous established TOPK knockdown clones to perform side population assay, ALDH activity assay and tumor sphere formation assay as described above. Interestingly, knockdown of TOPK significantly decreased the characteristics of cancer stem cells, such as decrease in SP cells, ALDH+ cells and tumor sphere formation (FIG. 10).

11. H2AX is Identified as an Interacting Protein of TOPK in M Phase Cells

To search for potential substrates of TOPK, we have previously performed GST-TOPK and GST-TOPK (KD; kinase-dead) pull down assay in asynchronized and M phase arrest HeLa cells. Specific interacting proteins were isolated and identified by LC/Mass/Mass. H2AX is one of the candidates that show apparent interaction with TOPK in M phase cells (data not shown). To validate the interaction of TOPK and H2AX, we transiently transfected Flag-TOPK-WT and Flag-TOPK-KD expression plasmids respectively into 293T or H1299 cells and analyzed their interactions by performing immunoprecipitation. As shown in FIG. 11, H2AX interacted with TOPK in M phase cells, while fairly weak interaction was detected in asynchronized cells. Since TOPK was phosphorylated and activated in M phase, the interactions of H2AX and TOPK in M phase suggest that H2AX may be a substrate of TOPK.

12. Knockdown of TOPK Decreases Cisplatin-Induced γ-H2AX and Sensitizes Cisplatin-Induced Cell Death Using GST pull-down and LC/Mass/Mass, we have identified H2AX as a putative TOPK interacting protein. Subsequently, we validated their interaction in M phase cell lysates (FIG. 11). H2AX is one of several genes coding for histone H2A. Thus, the H2AX protein contributes to the histone-formation and therefore the structure of DNA. H2AX becomes phosphorylated on serine 139, which is called gamma-H2AX (γ-H2AX), as a reaction on DNA double-strand breaks (DSB). The role of the phosphorylated form of the histone in DNA repair is not fully understood. But it is known that because of the modification, the DNA becomes less condensed. Since TOPK can interact with H2AX and may affect its phosphorylation, we therefore propose to examine whether the presence of TOPK will affect DNA damage response, such as cisplatin induced H2AX phosphorylation followed by cell death in lung cancer cells.

Platinum-based combination chemotherapy (i.e. cisplatin) is recognized as the first-line standard of care in NSCLC. The effects of cisplatin are mediated through high levels of DNA damage, leading to apoptosis or cell cycle arrest. To evaluate the role of TOPK in DNA damage response, we therefore examined γ-H2AX expression in cisplatin treated lung cancer cells. A549 cells were transiently transfected with TOPK siRNA. Forty-eight hr post-transfection, cells were treated with cisplatin for different time periods as indicated in FIG. 12A. Under the treatment of 35 μM cisplatin, which is the concentration that is found in the serum of cisplatin-treated patients,[87] γ-H2AX is induced and reached the peak at 12 hr in control cells (FIG. 12B). In addition, knockdown of TOPK by siRNA significantly decreased cisplatin-induced γ-H2AX in A549 cells. Similar results can be demonstrated in TOPK shRNA stably transfected cells (FIG. 12C). These results indicate TOPK may have a role in sustaining cisplatin-induced H2AX phosphorylation.

Since decrease in cisplatin-induced H2AX phosphorylation may indicate the less effective DNA damage repair, we therefore examined whether this decrease may correlate with higher cytotoxicity in responding to cisplatin treatment. We performed similar experiment as shown in FIG. 12A, and analyzed the cell viabilities after 48 hr of cisplatin treatment. As shown in FIG. 13, cisplatin conducted more cell death in TOPK knockdown cells as compared to control cells (sh-TOPK-3, shTOPK-4 vs. shNC: 16.2%, 13.6% vs. 25.7%), indicating TOPK could play a role in DNA damage response possibly by maintaining γ-H2AX associated DNA damage repair, which may affect the following cell death.

13. Knockdown of TOPK Promotes Cisplatin-Induced Cytotoxicity in Different Lung Cancer Cells Different lung cancer cell lines have been previously analyzed for the expression level of TOPK (data not shown). We have respectively selected high and low TOPK expression cells for overexpression or knockdown of TOPK and examined their sensitivity in response to cisplatin treatment. Recently, we have tested the knockdown effect of TOPK in promoting cisplatin-induced cytotoxicity in other lung cancer cells, such as CL152 and CL141 cells. Although cisplatin induced almost 90% of cell death in CL152 cells, knockdown of TOPK further enhanced the cytotoxic effect of cisplatin on these cells (FIG. 14). Our results suggest that TOPK mediated protective effect in response to cisplatin treatment may not be a cell-type specific effect. In addition, we also demonstrated that knockdown of TOPK decreased EGF-induced AKT phosphorylation (FIG. 15), suggesting that the expression level of TOPK may also have effect on cells resistant to gefitinib, a inhibitor of epidermal growth factor receptor's (EGFR) tyrosine kinase domain, such as PC9 and PC9/GR (EGFR-mutant exon 19 (T790M); gefitinib-resistant) cells.

II. Clinicopathological Data and Tissue Microarray Construction

Materials and Methods

From 1995 to 2007, 214 patients with stage I adenocarcinoma collected from the surgical pathology archives at Taipei Veterans General Hospital were enrolled in the study. All patients underwent curative surgical resection, accompanied by complete hilar and mediastinal lymph nodes dissection. No patient received adjuvant chemotherapy or radiotherapy after surgical resection. The pathological slides were reviewed by two pathologists (T.-Y.C. and Y.-C.Y.). The following pathological parameters were evaluated: tumor size, degree of tumor differentiation, tumor necrosis, and angiolymphatic invasion. Representative parts of the tumor tissue were selected for tissue microarray construction, which contained at least two 3-mm cores of tumor tissue retrieved from the paraffin blocks of each case. Overall survival of the patients was calculated from the date of operation to the date of death, and was considered censored for patients alive at last follow-up. Recurrence-free survival was measured from the date of operation up to the date of recurrence (either local or distant), and was considered censored for patients who were disease-free at last follow-up or dead without evidence of disease recurrence.

Immunohistochemistry (IHC) Staining and Scoring

The specimen processing and immunohistochemistry procedures were performed as previously described.[27] Five-micrometer-thick sections were made from the tissue microarrays. For TOPK IHC staining, a monoclonal antibody to TOPK (Cell Signaling) was used at the dilution of 1:100 and incubated for 1 hour. Then the sections were incubated with a biotinylated secondary antibody for 10 min. Streptavidin-horseradish peroxidase conjugate (DAKO LSAB kit; DAKO, Los Angles, Calif., USA) with 3-amino-9-ethylcarbazole was used as the chromogen. Finally, all slides were counterstained with haematoxylin.

The intensity of immunoreactivity was graded as following: 0 (negative), 1 (weakly positive), 2 (moderately positive), and 3 (strongly positive) (see FIG. 16). The percentage score was semiquantitatively assessed by percentage of positive-stained cells: 0 (0%), 1 (<=10%), 2 (11 to 50%), and 3 (51 to 100%). The IHC score of each specimen was recorded as the product of intensity score and percentage score, which ranged from 0 to 9.

Statistical Analysis

The Chi-square test was used to assess the association between clinicopathological parameters and TOPK IHC score. For survival analyses, the following variables were assessed: age, sex, smoking status, tumor size, tumor differentiation, tumor necrosis, angiolymphatic invasion, and TOPK IHC score. Survival curves were plotted with the Kaplan-Meier method and were compared using the log-rank test. Univariate and multivariate analyses were performed by means of the Cox proportional hazards model using SPSS software (version 18.0; SPSS, Chicago, Ill., USA). Statistical analysis was considered to be significant when $p<0.05$.

Results

The mean follow-up time was 61.5 months, with a range of 0.2 to 126 months. The demographic characteristics of these 214 patients are summarized in Table 4.

TABLE 4

Association of TOPK IHC score and clinicopathological characteristics

| Parameters | TOPK IHC score <=3 (n = 69) | TOPK IHC score >3 (n = 145) | P-value |
|---|---|---|---|
| Age, years | | | |
| Mean (±S.D.) | 65.3 (±10.6) | 65.2 (±11.0) | NS (0.946)* |
| Range | 29-87 | 34-88 | |
| Sex | | | |
| Male | 45 (65.2%) | 87 (60.0%) | NS (0.463)** |
| Female | 24 (34.8%) | 58 (40.0%) | |
| Smoking status | | | |
| Non-smoker | 30 (49.2%) | 64 (49.2%) | NS (0.995)** |
| Smoker | 31 (50.8%) | 66 (50.8%) | |
| Follow-up time, months | | | |
| Mean (±S.D.) | 76.9 (±30.0) | 54.2 (±30.0) | <0.001* |
| Range | 0.37-126 | 0.23-125.47 | |
| Recurrence status | | | |
| No recurrence | 54 (78.3%) | 95 (65.5%) | NS (0.058)** |
| Recurrence | 15 (21.7%) | 50 (34.5%) | |
| Tumor size, cm | | | |
| Mean (±S.D.) | 3.18 (±1.26) | 3.19 (±1.23) | NS (0.963)* |
| Range | 1-6 | 1-7 | |
| Tumor differentiation | | | |
| Well to moderate | 47 (68.1%) | 96 (66.2%) | NS (0.782)** |
| Poor | 22 (31.9%) | 49 (33.8%) | |
| Tumor necrosis | | | |
| No | 41 (59.4%) | 69 (47.6%) | NS (0.105)** |
| Yes | 28 (40.6%) | 76 (52.4%) | |
| Angiolymphatic invasion | | | |
| No | 54 (78.3%) | 92 (63.4%) | 0.030** |
| Yes | 15 (21.7%) | 53 (36.6%) | |

*t test;
**Chi-Square test;
NS: not significant

During the follow-up period, 65 (30.4%) patients developed tumor recurrence (local recurrence in 21 patients, distant metastasis in 55 patients).

The TOPK immunohistochemical staining was detected in the cytoplasm of tumor cells. Among the 214 patients, TOPK IHC score was distributed as following: 0 in 31 patients, 1 in 14 patients, 2 in 15 patients, 3 in 9 patients, 4 in 15 patients, 6 in 73 patients, and 9 in 57 patients. Sixty-nine (32.2%) patients had TOPK IHC score lower or equal to 3, while the remaining 145 (67.8%) patients had TOPK IHC score greater than 3. TOPK IHC score greater than 3 was considered as TOPK overexpression.

We investigated the association of various clinicopathological parameters with TOPK MC score <=3 and TOPK IHC score >3. The mean follow-up time was significantly shorter in patients with TOPK IHC score >3 ($p<0.001$). Angiolymphatic invasion was more frequently identified in patients with TOPK IHC score >3 ($p=0.030$). As shown in Table 5, there was no significant association in other clinicopathological parameters with TOPK expression.

Furthermore, we analyzed the prognostic value of age, sex, smoking status, tumor size, pathological tumor differentiation, tumor necrosis, angiolymphatic invasion and TOPK IHC score on overall survival of the patients. The overall survival was significantly worse in patients older than 65 years old (p=0.001), with tumor size >3 cm (p=0.013), presence of tumor necrosis (p=0.001), presence of angiolymphatic invasion (p=0.003), and TOPK IHC score >3 (p<0.001) (see Table 5).

TABLE 5

Five-year overall survival rates stratified by various clinicopathologic parameters

| Clinicopathologic parameters | 5-year survival rate ± SE (%) | Log-Rank P-value |
|---|---|---|
| Age, years | | |
| <=65 | 73.2 ± 4.8 | 0.001 |
| >65 | 53.2 ± 4.5 | |
| Sex | | |
| Male | 57.5 ± 4.3 | NS (0.238) |
| Female | 67.7 ± 5.4 | |
| Smoking status | | |
| Non-smoker | 65.6 ± 4.9 | NS (0.200) |
| Smoker | 54.6 ± 5.1 | |
| Tumor size, cm | | |
| <=3 | 67.4 ± 4.3 | 0.013 |
| >3 | 52.6 ± 5.4 | |
| Tumor differentiation | | |
| Well to moderate | 65.6 ± 4.0 | NS (0.106) |
| Poor | 52.5 ± 6.0 | |
| Tumor necrosis | | |
| Yes | 51.0 ± 5.0 | 0.001 |
| No | 71.0 ± 4.4 | |
| Angiolymphatic invasion | | |
| Yes | 46.6 ± 6.1 | 0.003 |
| No | 68.3 ± 3.9 | |
| TOPK IHC Score | | |
| <=3 | 82.5 ± 4.6 | <0.001 |
| >3 | 50.9 ± 4.3 | |

NS: not significant

The Kaplan-Meier overall survival curves for patient with TOPK IHC score <=3 and >3 were shown in FIG. 17. Multivariate Cox regression analyses revealed that age order than 65 years old (hazard ratio [HR]=2.21; 95% confidence interval [CI], 1.39 to 3.53, p=0.001) and TOPK IHC Score >3 (HR=3.46; 95% CI, 1.98 to 6.04; p<0.001) were independent predictors of overall survival (see Table 6).

TABLE 6

Multivariate analyses for overall survival

| Clinicopathologic parameters | Hazard Ratio | 95% Confidence Interval | P-value |
|---|---|---|---|
| Age >65 years old | 2.21 | 1.39-3.53 | 0.001 |
| Female | 0.88 | 0.49-1.56 | NS (0.666) |
| Smoking history | 0.93 | 0.53-1.64 | NS (0.827) |
| Tumor size >3 cm | 1.37 | 0.90-2.08 | NS (0.142) |
| Poor differentiation | 1.18 | 0.74-1.91 | NS (0.474) |
| Necrosis | 1.14 | 0.69-1.88 | NS (0.591) |

TABLE 6-continued

Multivariate analyses for overall survival

| Clinicopathologic parameters | Hazard Ratio | 95% Confidence Interval | P-value |
|---|---|---|---|
| Angiolymphatic invasion | 1.49 | 0.96-2.30 | NS (0.071) |
| TOPK IHC Score >3 | 3.46 | 1.98-6.04 | <0.001 |

NS: not significant

We further analyzed the prognostic factors for recurrence free survival. Tumor size >3 cm (p=0.007), poor differentiation (p=0.013), presence of tumor necrosis (p=0.001) and TOPK IHC score >3 (p=0.026) were associated with poor recurrence-free survival (Table 7).

TABLE 7

Five-year recurrence-free survival rates stratified by various clinicopathologic parameters

| Clinicopathologic parameters | 5-year recurrence-free survival rate ± SE (%) | Log-Rank P-value |
|---|---|---|
| Age, years | | |
| <=65 | 73.9 ± 4.7 | NS (0.129) |
| >65 | 62.6 ± 4.6 | |
| Sex | | |
| Male | 67.3 ± 4.3 | NS (0.856) |
| Female | 67.6 ± 5.4 | |
| Smoking status | | |
| Non-smoker | 67.5 ± 5.0 | NS (0.958) |
| Smoker | 67.6 ± 5.0 | |
| Tumor size, cm | | |
| <=3 | 74.5 ± 4.0 | 0.007 |
| >3 | 57.5 ± 5.5 | |
| Tumor differentiation | | |
| Well to moderate | 72.2 ± 3.9 | 0.013 |
| Poor | 58.0 ± 6.1 | |
| Tumor necrosis | | |
| Yes | 57.6 ± 5.0 | 0.001 |
| No | 76.8 ± 4.2 | |
| Angiolymphatic invasion | | |
| Yes | 59.1 ± 6.2 | NS (0.063) |
| No | 71.4 ± 3.9 | |
| TOPK IHC Score | | |
| <=3 | 77.9 ± 5.0 | 0.026 |
| >3 | 62.3 ± 4.3 | |

NS: not significant

The Kaplan-Meier recurrence-free survival curves for patient with TOPK IHC score <=3 and TOPK IHC score >3 were shown in FIG. 18. Only TOPK IHC score >3 (HR=2.25, 95% CI, 1.14 to 4.44, p=0.019) remained to be an independent predictor of recurrence-free survival upon multivariate Cox regression analyses (Table 8).

TABLE 8

Multivariate analysis for recurrence-free survival

| Clinicopathologic parameters | Hazard Ratio | 95% Confidence Interval | P-value |
|---|---|---|---|
| Age >65 years old | 1.61 | 0.89-2.89 | NS (0.109) |
| Female | 1.06 | 0.53-2.11 | NS (0.852) |
| Smoking history | 0.79 | 0.39-1.58 | NS (0.510) |
| Tumor size >3 cm | 1.48 | 0.86-2.54 | NS (0.155) |

TABLE 8-continued

Multivariate analysis for recurrence-free survival

| Clinicopathologic parameters | Hazard Ratio | 95% Confidence Interval | P-value |
|---|---|---|---|
| Poor differentiation | 1.55 | 0.86-2.79 | NS (0.142) |
| Necrosis | 1.30 | 0.69-2.46 | NS (0.410) |
| Angiolymphatic invasion | 1.33 | 0.77-2.28 | NS (0.302) |
| TOPK IHC Score >3 | 2.25 | 1.14-4.44 | 0.019 |

NS: not significant

In conclusion, overexpression of TOPK, either alone or in combination with a low level of PTEN, can serve as a significant prognostic marker to predict shortened overall and recurrence-free survivals in patients with resected stage I adenocarcinoma. The use of TOPK may help to identify high risk patients of stage I adenocarcinoma after surgical resection for adjuvant therapy or closer follow-up.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

REFERENCES

1. Spira A, Ettinger D S. Multidisciplinary management of lung cancer. N Engl J Med 2004; 350: 379-392.
2. Scott W J, Howington J, Feigenberg S, et al. Treatment of Non-small Cell Lung Cancer Stage I and Stage II: ACCP Evidence-Based Clinical Practice Guidelines (2nd Edition). Chest 2007; 132: 234S-242S.
3. Mountain C F. Revisions in the international system for staging lung cancer. Chest 1997; 111: 1710-1717.
4. Nesbitt J C, Putnam J B Jr, Walsh G L, et al. Survival in early-stage non-small cell lung cancer. Ann Thorac Surg 1995; 60: 466-472.
5. Martini N, Bains M S, Burt M E, et al. Incidence of local recurrence and second primary tumors in resected stage I lung cancer. J Thorac Cardiovasc Surg 1995; 109: 120-129.
6. Harpole D H Jr, Herndon J E H, Young W G Jr, et al. Stage I non-small cell lung cancer. Cancer 1995; 76: 787-796.
7. Al-Kattan K, Sepsas E, Fountain S W, et al. Disease recurrence after resection for stage I lung cancer. Eur J Cardiothorac Surg 1997; 12: 380-384.
8. Hung J J, Hsu W H, Hsieh C C, et al. Post-recurrence survival in completely resected stage I non-small cell lung cancer with local recurrence. Thorax 2009; 64: 192-196.
9. Hung J J, Jeng W J, Hsu W H, et al. Prognostic factors of post-recurrence survival in completely resected stage I non-small cell lung cancer with distant metastasis. Thorax 2010; 65: 241-245.
10. Sugimura H, Nichols F C, Yang P, et al. Survival after recurrent nonsmall-cell lung cancer after complete pulmonary resection. Ann Thorac Surg 2007; 83: 409-418.
11. Williams B A, Sugimura H, Endo C, et al. Predicting postrecurrence survival among completely resected nonsmall-cell lung cancer patients. Ann Thorac Surg. 2006; 81: 1021-1027.
12. Yoshino I, Yohena T, Kitajima M, et al. Survival of non-small cell lung cancer patients with postoperative recurrence at distant organs. Ann Thorac Cardiovasc Surg 2001; 7: 204-209.
13. Strauss G M, Herndon J E II, Maddaus M A, et al. Adjuvant paclitaxel plus carboplatin compared with observation in stage IB non-small-cell lung cancer: CALGB 9633 with the Cancer and Leukemia Group B, Radiation Therapy Oncology Group, and North Central Cancer Treatment Group Study Groups. J Clin Oncol 2008; 26: 5043-5051.
14. Pignon J P, Tribodet H, Scagliotti G V, et al. Lung adjuvant cisplatin evaluation: a pooled analysis by the LACE Collaborative Group. J Clin Oncol 2008; 26: 3552-3559.
15. Butts C A, Ding K, Seymour L, et al. Randomized phase III trial of vinorelbine plus cisplatin compared with observation in completely resected stage IB and II non-small-cell lung cancer: updated survival analysis of JBR-10. J Clin Oncol 2010; 28: 29-34.
16. Abe Y, Matsumoto S, Kito K, et al. Cloning and expression of a novel MAPKK-like protein kinase, lymphokine-activated killer T-cell-originated protein kinase, specifically expressed in the testis and activated lymphoid cells. J Biol Chem 2000; 275: 21525-21531.
17. Gaudet S, Branton D, Lue R A. Characterization of PDZ-binding kinase, a mitotic kinase. Proc Natl Acad Sci USA 2000; 97: 5167-5172.
18. Nandi A, Tidwell M, Karp J, et al. Protein expression of PDZ-binding kinase is up-regulated in hematologic malignancies and strongly down-regulated during terminal differentiation of HL-60 leukemic cells. Blood Cells Mol Dis 2004; 32: 240-245.
19. Park J H, Lin M L, Nishidate T, et al. PDZ-binding kinase/T-LAK cell-originated protein kinase, a putative cancer/testis antigen with an oncogenic activity in breast cancer. Cancer Res 2006; 66: 9186-9195.
20. Simons-Evelyn M, Bailey-Dell K, Toretsky J A, et al. PBK/TOPK is a novel mitotic kinase which is upregulated in Burkitt's lymphoma and other highly proliferative malignant cells. Blood Cells Mol Dis 2001; 27: 825-829.
21. Zhu F, Zykova T A, Kang B S, et al. Bidirectional signals transduced by TOPK-ERK interaction increase tumorigenesis of HCT116 colorectal cancer cells. Gastroenterology 2007; 133: 219-231.
22. Zykova T A, Zhu F, Lu C, et al. Lymphokine-activated killer T-cell-originated protein kinase phosphorylation of histone H2AX prevents arsenite-induced apoptosis in RPMI7951 melanoma cells. Clin Cancer Res 2006; 12: 6884-6893.
23. Ayllon V, O'Connor R. PBK/TOPK promotes tumour cell proliferation through p38 MAPK activity and regulation of the DNA damage response. Oncogene 2007; 26: 3451-3461.
24. Oh S M, Zhu F, Cho Y Y, et al. T-lymphokine-activated killer cell-originated protein kinase functions as a positive regulator of c-Jun-NH2-kinase 1 signaling and H-Ras-induced cell transformation. Cancer Res 2007; 67: 5186-5194.
25. Hu F, Gartenhaus R B, Eichberg D, et al. PBK/TOPK interacts with the DBD domain of tumor suppressor p53 and modulates expression of transcriptional targets including p21. Oncogene. 2010; 29: 5464-5474.
26. Nandi A K, Ford T, Fleksher D, et al. Attenuation of DNA damage checkpoint by PBK, a novel mitotic kinase, involves protein-protein interaction with tumor suppressor p53. Biochem Biophys Res Commun 2007; 358: 181-188.
27. Hung J J, Yang M H, Hsu H S, et al. Prognostic significance of hypoxia-inducible factor-1□, TWIST1 and Snail expression in resectable non-small cell lung cancer. Thorax 2009; 64: 1082-1089.

28. Youlden D R, Cramb S M, Baade P D. The International Epidemiology of Lung Cancer: geographical distribution and secular trends. J Thorac Oncol 2008; 3: 819-831.

29. Devesa S S, Bray F, Vizcaino A P, et al. International lung cancer trends by histologic type: male:female differences diminishing and adenocarcinoma rates rising. Int J Cancer 2005; 117: 294-299.

30. Langer C J, Besse B, Gualberto A, et al. The evolving role of histology in the management of advanced non-small-cell lung cancer. J Clin Oncol 2010; 28: 5311-5320.

31. Hirsch F R, Spreafico A, Novello S, et al. The prognostic and predictive role of histology in advanced non-small cell lung cancer: A literature review. J Thorac Oncol 2008; 3: 1468-1481.

32. Johnson D H, Fehrenbacher L, Novotny W F, et al. Randomized phase II trial comparing bevacizumab plus carboplatin and paclitaxel with carboplatin and paclitaxel alone in previously untreated locally advanced or metastatic non-small-cell lung cancer. J Clin Oncol 2004; 22: 2184-2191.

33. Scagliotti G, Hanna N, Fossella F, et al. The differential efficacy of pemetrexed according to NSCLC histology: A review of two phase III studies. Oncologist 2009; 14: 253-263.

34. Lau S K, Boutros P C, Pintilie M, et al. Three-gene prognostic classifier for early-stage non small-cell lung cancer. J Clin Oncol 2007; 25: 5562-5569.

35. Chen H Y, Yu S L, Chen C H, et al. A five-gene signature and clinical outcome in non-small cell lung cancer. New Eng J Med 2007; 356: 11-20.

36. Lu Y, Lemon W, Liu P Y, et al. A gene expression signature predicts survival of patients with stage I non-small cell lung cancer. PLoS Med 2006; 3: e467.

37. Beer D G, Kardia S L R, Huang C C, et al. Gene-expression profiles predict survival of patients with lung adenocarcinoma. Nature Med 2002; 8: 816-823.

38. Bianchi F, Nuciforo P, Vecchi M, et al. Survival prediction of stage I lung adenocarcinomas by expression of 10 genes. J Clin Invest 2007; 117: 34-44.

39. Abe Y, Takeuchi T, Kagawa-Miki L, Ueda N, Shigemoto K, Yasukawa M et al (2007). A mitotic kinase TOPK enhances Cdk1/cyclin B1-dependent phosphorylation of PRC1 and promotes cytokinesis. J Mol Biol 370: 231-245.

40. Akca H, Demiray A, Tokgun O, Yokota J (2011). Invasiveness and anchorage independent growth ability augmented by PTEN inactivation through the PI3K/AKT/NFkB pathway in lung cancer cells. Lung Cancer.

41. Arriagada R, Bergman B, Dunant A, Le Chevalier T, Pignon J P, Vansteenkiste J (2004). Cisplatin-based adjuvant chemotherapy in patients with completely resected non-small-cell lung cancer. N Engl J Med 350: 351-360.

42. Arriagada R, Auperin A, Burdett S, Higgins J P, Johnson D H, Le Chevalier T et al (2010). Adjuvant chemotherapy, with or without postoperative radiotherapy, in operable non-small-cell lung cancer: two meta-analyses of individual patient data. Lancet 375: 1267-1277.

43. Chalhoub N, Baker S J (2009). PTEN and the PI3-kinase pathway in cancer. Annu Rev Pathol 4: 127-150.

44. Chen C H, Lai J M, Chou T Y, Chen C Y, Su L J, Lee Y C et al (2009a). VEGFA upregulates FLJ10540 and modulates migration and invasion of lung cancer via PI3K/AKT pathway. PLoS One 4: e5052.

45. Chen T C, Lee S A, Hong T M, Shih J Y, Lai J M, Chiou H Y et al (2009b). From midbody protein-protein interaction network construction to novel regulators in cytokinesis. J Proteome Res 8: 4943-4953.

46. Friedl P, Wolf K (2003). Tumour-cell invasion and migration: diversity and escape mechanisms. Nat Rev Cancer 3: 362-374.

47. Gibbs A R, Thunnissen F B (2001). Histological typing of lung and pleural tumours: third edition. J Clin Pathol 54: 498-499.

48. Herrero-Martin D, Osuna D, Ordonez J L, Sevillano V, Martins A S, Mackintosh C et al (2009). Stable interference of EWS-FLI1 in an Ewing sarcoma cell line impairs IGF-1/IGF-1R signalling and reveals TOPK as a new target. Br J Cancer 101: 80-90.

49. Hung J J, Hsu W H, Hsieh C C, Huang B S, Huang M H, Liu J S et al (2009). Post-recurrence survival in completely resected stage I non-small cell lung cancer with local recurrence. Thorax 64: 192-196.

50. Kratz J R, Jablons D M (2009). Genomic prognostic models in early-stage lung cancer. Clin Lung Cancer 10: 151-157.

51. Matsumoto S, Abe Y, Fujibuchi T, Takeuchi T, Kito K, Ueda N et al (2004). Characterization of a MAPKK-like protein kinase TOPK. Biochem Biophys Res Commun 325: 997-1004.

52. Omuro A M, Kris M G, Miller V A, Franceschi E, Shah N, Milton D T et al (2005). High incidence of disease recurrence in the brain and leptomeninges in patients with non-small cell lung carcinoma after response to gefitinib. Cancer 103: 2344-2348.

53. Soria J C, Lee H Y, Lee J I, Wang L, Issa J P, Kemp B L et al (2002). Lack of PTEN expression in non-small cell lung cancer could be related to promoter methylation. Clin Cancer Res 8: 1178-1184.

54. Strauss G M, Herndon J E, 2nd, Maddaus M A, Johnstone D W, Johnson E A, Harpole D H et al (2008). Adjuvant paclitaxel plus carboplatin compared with observation in stage IB non-small-cell lung cancer: CALGB 9633 with the Cancer and Leukemia Group B, Radiation Therapy Oncology Group, and North Central Cancer Treatment Group Study Groups. J Clin Oncol 26: 5043-5051.

55. Su L J, Chang C W, Wu Y C, Chen K C, Lin C J, Liang S C et al (2007). Selection of DDX5 as a novel internal control for Q-RT-PCR from microarray data using a block bootstrap re-sampling scheme. BMC Genomics 8: 140.

56. Sugimura H, Nichols F C, Yang P, Allen M S, Cassivi S D, Deschamps C et al (2007). Survival after recurrent nons-mall-cell lung cancer after complete pulmonary resection. Ann Thorac Surg 83: 409-417; discussioin 417-408.

57. Vivanco I, Sawyers C L (2002). The phosphatidylinositol 3-Kinase AKT pathway in human cancer. Nat Rev Cancer 2: 489-501.

58. Wang X, Trotman L C, Koppie T, Alimonti A, Chen Z, Gao Z et al (2007). NEDD4-1 is a proto-oncogenic ubiquitin ligase for PTEN. Cell 128: 129-139.

59. Zlobec I, Molinari F, Kovac M, Bihl M P, Alternatt H J, Diebold J et al (2010). Prognostic and predictive value of TOPK stratified by KRAS and BRAF gene alterations in sporadic, hereditary and metastatic colorectal cancer patients. Br J Cancer 102: 151-161.

60. Abe Y, Takeuchi T, Kagawa-Miki L, Ueda N, Shigemoto K, Yasukawa M et al (2007). A mitotic kinase TOPK enhances Cdk1/cyclin B1-dependent phosphorylation of PRC1 and promotes cytokinesis. J Mol Biol 370: 231-245.

61. Akca H, Demiray A, Tokgun O, Yokota J (2011). Invasiveness and anchorage independent growth ability augmented by PTEN inactivation through the PI3K/AKT/NaB pathway in lung cancer cells. Lung Cancer.

62. Arriagada R, Bergman B, Dunant A, Le Chevalier T, Pignon J P, Vansteenkiste J (2004). Cisplatin-based adjuvant chemotherapy in patients with completely resected non-small-cell lung cancer. *N Engl J Med* 350: 351-360.
63. Arriagada R, Auperin A, Burdett S, Higgins J P, Johnson D H, Le Chevalier T et al (2010). Adjuvant chemotherapy, with or without postoperative radiotherapy, in operable non-small-cell lung cancer: two meta-analyses of individual patient data. *Lancet* 375: 1267-1277.
64. Chalhoub N, Baker S J (2009). PTEN and the PI3-kinase pathway in cancer. *Annu Rev Pathol* 4: 127-150.
65. Chen C H, Lai J M, Chou T Y, Chen C Y, Su L J, Lee Y C et al (2009a). VEGFA upregulates FLJ10540 and modulates migration and invasion of lung cancer via PI3K/AKT pathway. *PLoS One* 4: e5052.
66. Chen T C, Lee S A, Hong T M, Shih J Y, Lai J M, Chiou H Y et al (2009b). From midbody protein-protein interaction network construction to novel regulators in cytokinesis. *J Proteome Res* 8: 4943-4953.
67. Friedl P, Wolf K (2003). Tumour-cell invasion and migration: diversity and escape mechanisms. *Nat Rev Cancer* 3: 362-374.
68. Gibbs A R, Thunnissen F B (2001). Histological typing of lung and pleural tumours: third edition. Clin Pathol 54: 498-499.
69. Herrero-Martin D, Osuna D, Ordonez J L, Sevillano V, Martins A S, Mackintosh C et al (2009). Stable interference of EWS-FLI1 in an Ewing sarcoma cell line impairs IGF-1/IGF-1R signalling and reveals TOPK as a new target. *Br J Cancer* 101: 80-90.
70. Hung J J, Hsu W H, Hsieh C C, Huang B S, Huang M H, Liu J S et al (2009). Post-recurrence survival in completely resected stage I non-small cell lung cancer with local recurrence. *Thorax* 64: 192-196.
71. Kratz J R, Jablons D M (2009). Genomic prognostic models in early-stage lung cancer. *Clin Lung Cancer* 10: 151-157.
72. Matsumoto S, Abe Y, Fujibuchi T, Takeuchi T, Kito K, Ueda N et al (2004). Characterization of a MAPKK-like protein kinase TOPK. *Biochem Biophys Res Commun* 325: 997-1004.
73. Omuro A M, Kris M G, Miller V A, Franceschi E, Shah N, Milton D T et al (2005). High incidence of disease recurrence in the brain and leptomeninges in patients with non-small cell lung carcinoma after response to gefitinib. *Cancer* 103: 2344-2348.
74. Soria J C, Lee H Y, Lee J I, Wang L, Issa J P, Kemp B L et al (2002). Lack of PTEN expression in non-small cell lung cancer could be related to promoter methylation. *Clin Cancer Res* 8: 1178-1184.
75. Strauss G M, Herndon J E, 2nd, Maddaus M A, Johnstone D W, Johnson E A, Harpole D H et al (2008). Adjuvant paclitaxel plus carboplatin compared with observation in stage IB non-small-cell lung cancer: CALGB 9633 with the Cancer and Leukemia Group B, Radiation Therapy Oncology Group, and North Central Cancer Treatment Group Study Groups. *J Clin Oncol* 26: 5043-5051.
76. Su L J, Chang C W, Wu Y C, Chen K C, Lin C J, Liang S C et al (2007). Selection of DDX5 as a novel internal control for Q-RT-PCR from microarray data using a block bootstrap re-sampling scheme. *BMC Genomics* 8: 140.
77. Sugimura H, Nichols F C, Yang P, Allen M S, Cassivi S D, Deschamps C et al (2007). Survival after recurrent nonsmall-cell lung cancer after complete pulmonary resection. *Ann Thorac Surg* 83: 409-417; discussioin 417-408.
78. Vivanco I, Sawyers C L (2002). The phosphatidylinositol 3-Kinase AKT pathway in human cancer. *Nat Rev Cancer* 2: 489-501.
79. Wang X, Trotman L C, Koppie T, Alimonti A, Chen Z, Gao Z et al (2007). NEDD4-1 is a proto-oncogenic ubiquitin ligase for PTEN. *Cell* 128: 129-139.
80. Zlobec I, Molinari F, Kovac M, Bihl M P, Alternatt H J, Diebold J et al (2010). Prognostic and predictive value of TOPK stratified by KRAS and BRAF gene alterations in sporadic, hereditary and metastatic colorectal cancer patients. *Br J Cancer* 102: 151-161.
81. Shih M C, Chen J Y, Wu Y C, Jan Y H, Yang B M, Lu P J, et al. TOPK/PBK promotes cell migration via modulation of the PI3K/PTEN/AKT pathway and is associated with poor prognosis in lung cancer. Oncogene. 2011 Sep. 26.
82. Wei D C, Yeh Y C, Hung J J, Chou T Y, Wu Y C, Lu P J, et al. Overexpression of TOPK predicts poor prognosis in patients with stage I lung adenocarcinoma. Cancer Sci. 2011 Dec. 22.
83. Shats I, Gatza M L, Chang J T, Mori S, Wang J, Rich J, et al. Using a stem cell-based signature to guide therapeutic selection in cancer. Cancer Res. 2011 Mar. 1; 71(5):1772-80.
84. Ho M M, Ng A V, Lam S, Hung J Y. Side population in human lung cancer cell lines and tumors is enriched with stem-like cancer cells. Cancer Res. 2007 May 15; 67(10): 4827-33.
85. Eramo A, Lotti F, Sette G, Pilozzi E, Biffoni M, Di Virgilio A, et al. Identification and expansion of the tumorigenic lung cancer stem cell population. Cell Death Differ. 2008 March; 15(3):504-14.
86. Jiang F, Qiu Q, Khanna A, Todd N R, Deepak J, Xing L, et al. Aldehyde dehydrogenase 1 is a tumor stem cell-associated marker in lung cancer. Mol Cancer Res. 2009 March; 7(3):330-8.
87. Dimanche-Boitrel M T, Meurette O, Rebillard A, Lacour S. Role of early plasma membrane events in chemotherapy-induced cell death. Drug Resist Updat. 2005 February-April; 8(1-2):5-14.
88. Lamb J, Crawford E D, Peck D, Modell J W, Blat I C, Wrobel M J, et al. The Connectivity Map: using gene-expression signatures to connect small molecules, genes, and disease. Science. 2006 Sep. 29; 313(5795):1929-35.

I claim:

1. A method for evaluating the prognostic value in a patient in the resected stage I lung adenocarcinoma comprising the steps of collecting a tissue sample from the patient, determining the level of TOPK expressed in the tissue sample, wherein the prognostic value of the patient is worst if the overexpression of TOPK in the patient's tissue sample is found.

2. The method of claim 1, wherein the TOPK expression is determined in terms of an Immunohistochemistry (IHC) score.

3. The method of claim 2, wherein the IHC score of the sample of a patient is larger than 3, the overall survival of the patient is worse.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: siTOPK-1

```
<400> SEQUENCE: 1
gcagccauaa uuuuaaaagt t                                              21

<210> SEQ ID NO 2
<211> LENGTH: 21
<212> TYPE: DNA
<213> ORGANISM: Artificial Sequence
<220> FEATURE:
<223> OTHER INFORMATION: siTOPK-2

<400> SEQUENCE: 2
cccugaggcu uguuacauut t                                              21

<210> SEQ ID NO 3
<211> LENGTH: 21
<212> TYPE: DNA
<213> ORGANISM: Artificial Sequence
<220> FEATURE:
<223> OTHER INFORMATION: shTOPK-3

<400> SEQUENCE: 3
tgaccctgag gcttgttaca t                                              21

<210> SEQ ID NO 4
<211> LENGTH: 21
<212> TYPE: DNA
<213> ORGANISM: Artificial Sequence
<220> FEATURE:
<223> OTHER INFORMATION: shTOPK-4

<400> SEQUENCE: 4
tgtgggaaat gatgacttta t                                              21
```